United States Patent
Eisenberg et al.

(10) Patent No.: US 7,177,766 B2
(45) Date of Patent: Feb. 13, 2007

(54) SELECTION OF SITES FOR TARGETING BY ZINC FINGER PROTEINS AND METHODS OF DESIGNING ZINC FINGER PROTEINS TO BIND TO PRESELECTED SITES

(75) Inventors: Stephen Eisenberg, Boulder, CO (US); Casey Case, San Mateo, CA (US); George Cox, III, Louisville, CO (US); Andrew Jamieson, San Francisco, CA (US); Edward Rebar, Berkeley, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 814 days.

(21) Appl. No.: 09/825,242

(22) Filed: Apr. 2, 2001

(65) Prior Publication Data
US 2003/0092000 A1 May 15, 2003

Related U.S. Application Data

(62) Division of application No. 09/229,007, filed on Jan. 12, 1999, now Pat. No. 6,453,242.

(51) Int. Cl.
G06F 19/00 (2006.01)
G06G 7/60 (2006.01)
C07K 14/00 (2006.01)
C12N 15/11 (2006.01)

(52) U.S. Cl. .................. 702/19; 703/11; 530/387.3; 536/23.4

(58) Field of Classification Search ............ 702/19; 435/6; 530/350; 536/23.1
See application file for complete search history.

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |

FOREIGN PATENT DOCUMENTS

| | | |
|---|---|---|
| EP | 875 567 A2 | 4/1998 |
| EP | 875 567 | 11/1998 |

(Continued)

OTHER PUBLICATIONS

Corbi et al. Synthesis of a new zinc finger peptide; comparison of its 'code' deduced and 'CASTing' derived binding sites. FEBS Letters, vol. 417, pp. 71-74 (1997).*

(Continued)

*Primary Examiner*—John S. Brusca
(74) *Attorney, Agent, or Firm*—Townsend and Townsend and Crew, LLP

(57) ABSTRACT

The invention provides criteria and methods for selecting optimum subsequence(s) from a target gene for targeting by a zinc finger protein. Some of the methods of target site selection seek to identify one or more target segments having a DNA motif containing one or more so-called D-able subsites having the sequence 5'NNGK3'. Other methods of the invention are directed to selection of target segments within target genes using a correspondence regime between different triplets of three bases and the three possible positions of a triplet within a nine-base site. In another aspect, the invention provides methods of designing zinc finger proteins that bind to a preselected target site. These methods can be used following the preselection of target sites according to the procedures and criteria described above. The methods of design use a database containing information about previously characterized zinc finger proteins.

11 Claims, 10 Drawing Sheets

FOREIGN PATENT DOCUMENTS

| | | |
|---|---|---|
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |

OTHER PUBLICATIONS

Isalan et al. comprehensive DNA recognition through Concerted Interactions from Adjacent Zinc Fingers. Biochemistry, vol. 37, pp. 12026-12033 (1998).*

Agarwal et al., "Stimulation of Transcript Elongation Requires both the Zinc Finger and RNA Polymerase II Binding Domains of Human TFIIS," *Biochemistry*, 30(31):7842-7851 (1991).

Anato et al., "A thermodynamic study of unusually stable RNA and DNA hairpins," *Nuc. Acids. Res.*, 19(21):5901-5905 (1991).

Barbas, C. F., "Recent advances in phage display," *Curr. Opin. Biotech.*, 4:526-530 (1993).

Barbas et al., "Assembly of combinatorial antibody libraries on phage surfaces: The gene III site," *PNAS*, 88:7978-7982 (1991).

Barbas et al., "Semisynthetic combinatorial antibody libraries: A chemical solution to the diversity problem," *PNAS*, 89:4457-4461 (1992).

Beerli et al., "Toward controlling gene expression at will: Specific regulation of the *erbB-2/HER-2* promoter by using polydactyl zinc finger proteins constructed from modular building blocks," *PNAS*, 95:14628-14633 (1998).

Bellefroid et al., "Clustered organization of homologous KRAB zinc-finger genes with enhanced expression in human T lymphoid cells," *EMBO J.*, 12(4):1363-1374 (1993).

Berg, J. M., "DNA Binding Specificity of Steriod Receptors," *Cell*, 57:1065-1068 (1989).

Berg, J. M., "Sp1 and the subfamily of zinc finger proteins with guanine-rich binding sites," *PNAS*, 89:11109-11110 (1992).

Berg et al., "The Galvanization of Biology: A Growing Appreciation for the Roles of Zinc," *Science*, 271:1081-1085 (1996).

Berg, J.M., "Letting your fingers do the walking," *Nature Biotechnology*, 15:323 (1997).

Bergqvist et al., "Loss of DNA-binding and new transcriptional *trans*-activation function in polyomavirus large T-antigen with mutation of zinc finger motif," *Nuc. Acids Res.*, 18(9):2715-2720 (1990).

Blaese et al., "Vectors in cancer therapy: how will they deliver?," *Cancer Gene Therapy*, 2(4):291-297 (1995).

Caponigro et al., "Transdominant gentic analysis of a growth control pathway," *PNAS*, 95:7508-7513 (1998).

Celenza et al., "A Yeast Gene That Is Essential for Release from Glucose Repression Encodes a Protein Kinase," *Science*, 233:1175-1180 (1986).

Cheng et al., "Identification of Potential Target Genes for Adr1p through Characterization of Essential Nucleotides in UAS1," *Mol. Cellular Biol.*, 14(6):3842-3852 (1994).

Cheng et al., "A Single Amino Acid substitution in Zinc Finger 2 of Adr1p Changes its Binding Specificity at two Positions in UAS1," *J. Mol. Biol.*, 251:1-8 (1995).

Choo et al., "A role in DNA binding for the linker sequences of the first three zinc fingers of TFIIIA," *Nuc. Acids Res.*, 21(15):3341-3346 (1993).

Choo et al., "Designing DNA-binding proteins on the surface of filamentous phage," *Curr. Opin. Biotechnology*, 6:431-436 (1995).

Choo et al., "Promoter-specific Activation of Gene Expression Directed by Bacteriophage-selected Zinc Fingers," *J. Mol. Biol.*, 273:525-532 (1997).

Choo, Y., "Recognition of DNA methylation by zinc fingers," *Nature Struct. Biol.*, 5(4):264-265 (1998).

Choo et al., "All wrapped up," *Nature Structural Biology*, 5(4):253-255 (1998).

Choo, Y., "End effects in DNA recognition by zinc finger arrays," *Nuc. Acids Res.*, 26(2):554-557 (1998).

Choo et al., "In vivo repression by a site-specific DNA-binding protein designed against an oncogenic sequence," *Nature*, 372:642-645 (1994).

Choo et al., "Physical basis of a protein-DNA recognition code," *Curr. Opin. Struct. Biol.*, 7(1):117-125 (1997).

Choo et al., "Toward a code for the interactions of zinc fingers with DNA: Selection of randomized fingers displayed on phage," *PNAS*, 91:11163-11167 (1994).

Choo et al., "Selection of DNA binding sites for zinc fingers using rationally randomized DNA reveals coded interactions," *PNAS*, 91:11168-11172 (1994).

Clarke et al., "Zinc Fingers in *Caenorhabditis elegans*: Finding Families and Probing Pathways," *Science*, 282:2018-2022 (1998).

Corbi, N. et al., "Synthesis of a New Zinc Finger Peptide; Comparison of its 'Code' Deduced and 'CASTing' Derived Binding Sites," *FEBS Letters*, 417:71-74 (1997).

Crozatier et al., "Single Amino Acid Exchanges in Separate Domains of the Drosophila serendipity δ Zinc Finger Protein Cause Embryonic and Sex Biased Lethality," *Genetics*, 131:905-916 (1992).

Debs et al., "Regulation of Gene Expression *in Vivo* by Liposome-mediated Delivery of a Purified Transcription Factor*," *J. Biological Chemistry*, 265(18):10189-10192 (1990).

Desjarlais et al., "Length-encoded multiplex binding site determination: Application to zinc finger proteins," *PNAS*, 91:11099-11103 (1994).

Desjarlais et al., "Use of a zinc-finger consensus sequence framework and specificity rules to design specific DNA binding proteins," *PNAS*, 90:2256-2260 (1993).

Desjarlais et al., "Toward rules relating zinc finger protein sequences and DNA binding site preferences," *PNAS*, 89(16):7345-7349 (1992).

Desjarlais et al., "Redesigning the DNA-Binding Specificity of a Zinc Finger Protein: A Data Base-Guided Approach," *Proteins: Structure, Function, and Genetics*, 12(2):101-104 (1992).

DiBello et al., "The Drosophila *Broad-Complex*Encodes a Family of Related Proteins Containing Zinc Fingers," *Genetics*, 129:385-397 (1991).

Elrod-Erickson et al., "High-resolution structures of variant Zif268-DNA complexes: implications for understanding zinc finger-DNA recognition," *Structure*, 6(4):451-464 (1998).

Elrod-Erickson et al., "Zif268 protein-DNA complex refined at 1.6 Å: a model system for understanding zinc finger-DNA interactions," *Structure*, 4(10):1171-1180 (1996).

Fairall et al., "The crystal structure of a two zinc-finger peptide reveals an extension to the rules for zinc-finger/DNA recognition," *Nature*, 366:483-487 (1993).

Frankel et al., "Fingering Too Many Proteins," *Cell*, 53:675 (1988).

Friesen et al., "Phage Display of RNA Binding Zinc Fingers from Transcription Factor IIIA*," *J. Biological Chem.*, 272(17):10994-10997 (1997).

Friesen et al., "Specific RNA binding proteins constructed from zinc fingers," *Nature Structural Biology*, 5(7):543-546(1998).

Gogos et al., "Recognition of diverse sequences by class I zinc fingers: Asymmetries and indirect effects on specificity in the interaction between CF2II and A+T-rich sequence elements," *PNAS*, 93(5):2159-2164 (1996).

Gossen et al., "Tight control of gene expression in mammalian cells by tetracycline-responsive promoters," *PNAS*, 89:5547-5551 (1992).

Greisman et al., "A General Strategy for Selecting High-Affinity Zinc Finger Proteins for Diverse DNA Target Sites," *Science*, 275:657-661 (1997).

Hamilton et al., "Comparison of the DNA Binding Characteristics of the Related Zinc Finger Proteins WT1 and EGR1," *Biochemistry*, 37:2051-2058 (1998).

Hamilton et al., "High affinity binding sites for the Wilms' tumor suppressor protein WT1," *Nuc. Acids Res.*, 23(2):277-284 (1995).

Hanas et al., "Internal deletion mutants of *Xenopus* transcription factor IIIA," *Nuc. Acids Res.*, 17(23):9861-9870 (1989).

Hayes et al., "Locations of Contacts between Individual Zinc Fingers of *Xenopus laevis* Transcription Factor IIIA and the Internal Control Region of a 5S RNA Gene," *Biochemistry*, 31:11600-11605 (1992).

Heinzel et al., "A complex containing N-CoR, mSin3 and histone deacetylase mediates transcriptional repression," *Nature*, 387:43-48 (1997).

Hirst et al., "Discrimination of DNA response elements for thyroid hormone and estrogen is dependant on dimerization of receptor DNA binding domains," *PNAS*, 89:5527-5531 (1992).

Hoffman et al., "Structures of DNA-binding mutant zinc finger domains: Implications for DNA binding," *Protein Science*, 2:951-965 (1993).

Isalan et al., "Synergy between adjacent zinc fingers in sequence-specific DNA recognition," *PNAS*, 94(11):5617-5621 (1997).

Isalan et al., "Comprehensive DNA Recognition through Concerted Interactions from Adjacent Zinc Fingers," *Biochemistry*, 37:12026-12033 (1998).

Jacobs, G. H., "Determination of the base recognition positions of zinc fingers from sequence analysis," *EMBO J.*, 11(12):4507-4517 (1992).

Jamieson et al., "A zinc finger directory for high-affinity DNA recognition," *PNAS*, 93:12834-12839 (1996).

Jamieson et al., "*In Vitro* Selection of Zinc Fingers with Altered DNA-Binding Specificity," *Biochemistry*, 33(19):5689-5695 (1994).

Julian et al., "Replacement of His23 by Cys in a zinc finger of HIV-1 NCp7 led to a change in 1H NMR-derived 3D structure and to a loss of biological activity," *FEBS letters*, 331(1,2):43-48 (1993).

Kamiuchi et al., "New multi zinc finger protein: biosynthetic design and characteristics of DNA recognition," *Nucleic Acids Symposium Series*, 37:153-154 (1997).

Kang, J.S. et al., "Zinc Finger Proteins as Designer Transcription Factors," *J. Biol. Chem.*, 275(12):8742-8748 (2000).

Kim et al., "Serine at Position 2 in the DNA Recognition helix of a Cys2-His2 Zinc finger Peptide is Not, in General, Responsible for Base Recognition," *J. Mol. Biol.*, 252:1-5 (1995).

Kim et al., "Site-specific cleavage of DNA-RNA hybrids by zinc finger/Fok I cleavage domain fusions," *Gene*, 203:43-49 (1997).

Kim et al., "A 2.2 A° resolution crystal structure of a designed zinc finger protein bound to DNA," *Nat. Struct. Biol.*, 3(11):940-945 (1996).

Kim et al., "Getting a handhold on DNA: Design of poly-zinc finger proteins with femtomolar dissociation constants," *PNAS*, 95:2812-2817 (1998).

Kim et al., "Design of TATA box-binding protein/zinc finger fusions for targeted regulation of gene expression," *PNAS*, 94:3616-3620 (1997).

Kim et al., "Hybrid restriction enzymes: Zinc finger fusions to Fok I cleavage domain," *PNAS*, 93:1156-1160 (1996).

Kim et al., "Transcriptional repression by zinc finger peptides," *J. Biol. Chem.*, 272(4):29795-28000 (1997).

Kinzler et al., "The GLI gene is a member of the Kruppel family of zinc finger proteins," *Nature*, 332:371-4 (1988).

Kriwacki et al., "Sequence-specific recognition of DNA by zinc-finger peptides derived from the transcription factor Sp1," *PNAS*, 89:9759-9763 (1992).

Klug, A., "Zinc Finger Peptides for the Regulation of Gene Expression," *J. Mol. Biol.*, 293:215-218 (1999).

Klug, A., "Gene Regulatory Proteins and Their Interaction with DNA," *Ann. NY Acad. Sci.*, 758:143-160 (1995).

Klug et al., "Protein Motifs 5: Zinc Fingers," *FASEB J.*, 9:597-604 (1995).

Kothekar, V., "Computer simulation of zinc finger motifs from cellular nucleic acid binding protein and their interaction with consensus DNA sequences," *FEBS Letters*, 274(1-2):217-222 (1990).

Kulda et al., "The regulatory gene areI A mediating nitrogen metabolite repression in *Aspergillus nidulans*. Mutations affecting specificity of gene activation alter a loop residue of a putative zinc finger," *EMBO J.*, 9(5):1355-1364 (1990).

Laird-Offringa et al., "RNA-binding proteins tamed," *Nat. Structural Biol.*, 5(8):665-668 (1998).

Liu et al., "Design of polydactyl zinc-finger proteins for unique addressing within complex genomes," *PNAS*, 94(11):5525-5530 (1997).

Mandel-Gutfreund et al., "Quantitative parameters for amino acid-base interaction: implications for prediction of protein-DNA binding sites," *Nuc. Acids Res.*, 26(10):2306-2312 (1998).

Margolin et al., "Kruppel-associated boxes are potent transcriptional repression domains," *PNAS*, 91:4509-4513 (1994).

Mizushima et al., "pEF-BOS, a powerful mammalian expression vector," *Nuc. Acids Res.*, 18(17):5322 (1990).

Nakagama et al., "Sequence and Structural Requirements for High-Affinity DNA Binding by the WT1 Gene Product," *Molecular and Cellular Biology*, 15(3):1489-1498 (1995).

Nardelli et al., "Zinc finger-DNA recognition: analysis of base specificity by site-directed mutagenesis," *Nuc. Acids Res.*, 20(16):4137-4144 (1992).

Nardelli et al., "Base sequence discrimination by zinc-finger DNA-binding domains," *Nature*, 349:175-178 (1991).

Nekludova et al., "Distinctive DNA conformation with enlarged major groove is found in Zn-finger—DNA and other protein—DNA complexes," *PNAS*, 91:6948-6952 (1994).

Pabo et al., "Systematic Analysis of Possible Hydrogen Bonds between Amino Acid Side Chains and B-form DNA," *J. Bimolecular Struct. Dynamics*, 1:1039-1049 (1983).

Pabo et al., "Protein-DNA Recognition," *Ann. Rev. Biochem.*, 53:293-321 (1984).

Pabo, C. O., "Transcription Factors: Structural Families and Principals of DNA Recognition," *Ann. Rev. Biochem.*, 61:1053-1095 (1992).

Pavletich et al., "Crystal Structure of a Five-Finger GLI-DNA Complex: New Perspectives on Zinc Fingers," *Science*, 261:1701-1707 (1993).

Pavletich et al., "Zinc Finger-DNA Recognition: Crystal Structure of a Zif268-DNA Complex at 2.1 Å," *Science*, 252:809-817 (1991).

Pengue et al., "Repression of transcriptional activity at a distance by the evolutionarily conserved KRAB domain present in a subfamily of zinc finger proteins," *Nuc. Acids Res.*, 22(15):2908-2914 (1994).

Pengue et al., "Transcriptional Silencing of Human Immunodeficiency Virus Type 1 Long Terminal Repeat-Driven Gene Expression by the Kruppel-Associated Box Repressor Domain Targeted to the Transactivating Response Element," *J. Virology*, 69(10):6577-6580 (1995).

Pengue et al., "Kruppel-associated box-mediated repression of RNA polymerase II promoters is influenced by the arrangement of basal promoter elements," *PNAS*, 93:1015-1020 (1996).

Pomerantz et al., "Structure-Based Design of a Dimeric Zinc Finger Protein," *Biochemistry*, 37(4):965-970 (1998).

Pomerantz et al., "Structure-Based Design of Transcription Factors," *Science*, 267:93-96 (1995).

Pomerantz et al., "Analysis of homeodomain function by structure-based design of a transcription factor," *PNAS*, 92:9752-9756 (1995).

Qian et al., "Two-Dimensional NMR Studies of the Zinc Finger Motif: Solution Structures and Dynamics of Mutant ZFY Domains Containing Aromatic Substitutions in the Hydrophobic Core," *Biochemistry*, 31:7463-7476 (1992).

Quigley et al., "Complete Androgen Insensitivity Due to Deletion of Exon C of the Androgen Receptor Gene Highlights the Functional Importance of the Second Zinc Finger of the Androgen Receptor *in Vivo,*" *Molecular Endocrinology*, 6(7):1103-1112 (1992).

Rauscher et al., "Binding of the Wilms' Tumor Locus Zinc Finger Protein to the EGR-1 Consensus Sequence," *Science*, 250:1259-1262 (1990).

Ray et al., "Repressor to activator switch by mutations in the first Zn finger of the glucocorticoid receptor: Is direct DNA binding necessary?," *PNAS*, 88:7086-7090 (1991).

Rebar et al., "Phage Display Methods for Selecting Zinc Finger Proteins with Novel DNA-Binding Specificities," *Methods in Enzymology*, 267:129-149 (1996).

Rebar et al., "Zinc Finger Phage: Affinity Selection of Fingers with New DNA-Binding Specificities," *Science*, 263:671-673 (1994).

Reith et al., "Cloning of the major histocompatibility complex class II promoter binding protein affected in a hereditary defect in class II gene regulation," *PNAS*, 86:4200-4204 (1989).

Rhodes et al., "Zinc Fingers: They play a key part in regulating the activity of genes in many species, from yeast to humans. Fewer than 10 years ago no one knew they existed," *Scientific American*, 268:56-65 (1993).

Rice et al., "Inhibitors of HIV Nucleocapsid Protein Zinc Fingers as Candidates for the Treatment of AIDS," *Science*, 270:1194-1197 (1995).

Rivera et al., "A humanized system for pharmacologic control of gene expression," *Nature Medicine*, 2(9):1028-1032 (1996).

Rollins et al., "Role of TFIIIA Zinc Fingers In vivo: Analysis of Single-Finger Function in Developing *Xenopus* Embryos," *Molecular Cellular Biology*, 13(8):4776-4783 (1993).

Saleh et al., "A Novel Zinc Finger Gene on Human Chromosome lqter That Is Alternatively Spliced in Human Tissues and Cell Lines," *Am. J. Hum. Genet.*, 52:192-203 (1993).

Shi et al., "Specific DNA-RNA Hybrid Binding by Zinc Finger Proteins," *Science*, 268:282-284 (1995).

Shi et al., "DNA Unwinding Induced by Zinc Finger Protein Binding," *Biochemistry*, 35:3845-3848 (1996).

Shi et al., "A direct comparison of the properties of natural and designed finger proteins," *Chem. & Biol.*, 2(2):83-89 (1995).

Singh et al., "Molecular Cloning of an Enhancer Binding Protein: Isolation by Screening of an Expression Library with a Recognition Site DNA," *Cell*, 52:415-423 (1988).

Skerka et al., "Coordinate Expression and Distinct DNA-Binding Characteristics of the four EGR-Zinc Finger Proteins in Jukat T Lymphocytes," *Immunobiology*, 198:179-191 (1997).

South et al., "The Nucleocapsid Protein Isolated from HIV-1 Particles Binds Zinc and Forms Retroviral-Type Zinc Fingers," *Biochemistry*, 29:7786-7789 (1990).

Suzuki et al., "Stereochemical basis of DNA recognition by Zn fingers," *Nuc. Acids Res.*, 22(16):3397-3405 (1994).

Suzuki et al., "DNA recognition code of transcription factors in the helix-turn-helix, probe helix, hormone receptor, and zinc finger families," *PNAS*, 91:12357-12361 (1994).

Swirnoff et al., "DNA-Binding Specificity of NGFI-A and Related Zinc Finger Transcription Factors," *Mol. Cell. Biol.*, 15(4):2275-2287 (1995).

Taylor et al, "Designing Zinc-Finer ADR1 Mutants with Altered Specificity of DNA Binding to T in UAS1 Sequences," *Biochemistry*, 34:3222-3230 (1995).

Thiesen et al., "Determination of DNA binding specificities of mutated zinc finger domains," *FEBS Letters*, 283(1):23-26 (1991).

Thiesen et al., "Amino Acid Substitutions in the SP1 Zinc Finger Domain Alter the DNA Binding Affinity to Cognate SP1 Target Site," *Biochem. Biophys. Res. Communications*, 175(1):333-338 (1991).

Thukral et al., "Localization of a Minimal Binding Domain and Activation Regions in Yeast Regulatory Protein ADR1," *Molecular Cellular Biology*, 9(6):2360-2369 (1989).

Thukral et al., "Two Monomers of Yeast Transcription Factor ADR1 Bind a Palindromic Sequence Symmetrically to Activate ADH2 Expression," *Molecular Cellular Biol.*, 11(3):1566-1577 (1991).

Thukral et al., "Alanine scanning site-directed mutagenesis of the zinc fingers of transcription factor ADR1:Residues that contact DNA and that transactivate," *PNAS*, 88:9188-9192 (1991), + correction page.

Thukral et al., "Mutations in the Zinc Fingers of ADR1 That Change the Specificity of DNA Binding and Transactivation," *Mol. Cell Biol.*, 12(6):2784-2792 (1992).

Vortkamp et al., "Identification of Optimized Target Sequences for the GLI3 Zinc Finger Protein," *DNA Cell Biol.*, 14(7):629-634 (1995).

Wang, S.W. et al., "Dimerization of Zinc fingers Mediated by Peptides Evolved *in vitro* from Random Sequences," *PNAS*, 96:9568-9573 (1999).

Webster et al., "Conversion of the E1A Cys4 zinc finger to a nonfunctional His2, Cys2 zinc finger by a single point mutation," *PNAS*, 88:9989-9993 (1991).

Whyatt et al., "The two zinc finger-like domains of GATA-1 have different DNA binding specificities," *EMBO J.*, 12(13):4993-5005 (1993).

Wilson et al., "*In Vivo* Mutational analysis of the NGFI-A Zinc Fingers*," *J. Biol. Chem.*, 267(6):3718-3724 (92).

Witzgall et al., "The Kruppel-associated box-A (KRAB-A) domain of zinc finger proteins mediates transcriptional repression," *PNAS*, 91:4514-4518 (1994).

Wolfe, S.A. et al., "Analysis of Zinc Fingers Optimized via Phage Display: Evaluating the Utility of a Recognition Code," *J. Mol. Biol.*, 285:1917-1934 (1999).

Wright et al., "Expression of a Zinc Finger Gene in HTLV-I- and HTLV-II-transformed Cells," *Science*, 248:588-591 (1990).

Wu et al., "Building zinc fingers by selection: Toward a therapeutic application," *PNAS*, 92:344-348 (1995).

Yang et al., "Surface plasmon resonance based kinetic studies of zinc finger-DNA interactions," *J. Immunol. Methods*, 183:175-182 (1995).

Yu et al., "A hairpin ribozyme inhibits expression of diverse strains of human immunodeficiency virus type 1," *PNAS*, 90:6340-6344 (1993).

Ghosh, D., "A relational database of transcription factors," *Nuc. Acids Res.*, 18(7):1749-1756 (1990).

Orkin et al., "Report and Recommendations of the Panel to Assess the NIH Investment in Research on Gene Therapy," Dec. 7, 1995, www.nih.gov/news/panelrep.html.

Sadowski et al., "GAL4-VP16 is an Unusually Potent Transcriptional Activator," *Nature*, 335:563-568 (1998).

Bonde et al., "Ontogeny of the v-erb A Oncoprotein from the Thyroid Hormone Receptor: an Alteration in the DNA Binding Domain Plays a Role Crucial for v-erb A Function," *J. Virology*, 65(4):2037-2046 (1991).

Desjardins et al., "Repeated CT Elements Bound by Zinc Finger Proteins Control the Absolute and Relative Activities of the Two Principal Human c-myc Promoters," *Mol. and Cellular Biol.*, 13(9):5710-5724 (1993).

Hall et al., "Functional Interaction between the Two Zinc finger Domains of the v-erb A Oncoprotein," *Clee Growth & Differentiation*, 3:207-216 (1992).

* cited by examiner

PCR amplification scheme for production of ZFP-encoding synthetic genes.

```
                              SEQUENCE LISTING

<160> NUMBER OF SEQ ID NOS: 97

<210> SEQ ID NO 1
  <211> LENGTH: 25
  <212> TYPE: PRT
  <213> ORGANISM: Artificial Sequence
  <220> FEATURE:
  <223> OTHER INFORMATION: Description of Artificial Sequence:exemplary
        motif characterizing the C-2H-2 class of zinc finger
        proteins (ZFP)
  <220> FEATURE:
  <221> NAME/KEY: MOD_RES
  <222> LOCATION: (1)..(25)
  <223> OTHER INFORMATION: Xaa = any amino acid
  <220> FEATURE:
  <221> NAME/KEY: MOD_RES
  <222> LOCATION: (4)..(5)
  <223> OTHER INFORMATION: Xaa = any amino acid, may be present or absent
  <220> FEATURE:
  <221> NAME/KEY: MOD_RES
  <222> LOCATION: (23)..(24)
  <223> OTHER INFORMATION: Xaa = any amino acid, may be present or absent

<400> SEQUENCE: 1

Cys Xaa Xaa Xaa Xaa Cys Xaa Xaa Xaa Xaa Xaa Xaa Xaa Xaa Xaa Xaa
   1               5                  10                  15

Xaa Xaa His Xaa Xaa Xaa Xaa Xaa His
              20                  25

<210> SEQ ID NO 2
  <211> LENGTH: 5
  <212> TYPE: PRT
  <213> ORGANISM: Artificial Sequence
  <220> FEATURE:
  <223> OTHER INFORMATION: Description of Artificial Sequence:peptide
        linker

<400> SEQUENCE: 2

Thr Gly Glu Lys Pro
   1               5

<210> SEQ ID NO 3
  <211> LENGTH: 5
  <212> TYPE: PRT
  <213> ORGANISM: Artificial Sequence
  <220> FEATURE:
  <223> OTHER INFORMATION: Description of Artificial Sequence:peptide
        linker

<400> SEQUENCE: 3

Gly Gly Gly Gly Ser
   1               5

<210> SEQ ID NO 4
  <211> LENGTH: 8
  <212> TYPE: PRT
  <213> ORGANISM: Artificial Sequence
  <220> FEATURE:
  <223> OTHER INFORMATION: Description of Artificial Sequence:peptide
        linker
```

```
<400> SEQUENCE: 4

Gly Gly Arg Arg Gly Gly Gly Ser
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:peptide
      linker

<400> SEQUENCE: 5

Leu Arg Gln Arg Asp Gly Glu Arg Pro
 1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:peptide
      linker

<400> SEQUENCE: 6

Leu Arg Gln Lys Asp Gly Gly Gly Ser Glu Arg Pro
 1               5                  10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence:peptide
      linker

<400> SEQUENCE: 7

Leu Arg Gln Lys Asp Gly Gly Gly Ser Gly Gly Gly Ser Glu Arg Pro
 1               5                  10                  15

<210> SEQ ID NO 8
<211> LENGTH: 85
<212> TYPE: PRT
<213> ORGANISM: Mus sp.
<220> FEATURE:
<223> OTHER INFORMATION: DNA binding domain of mouse transcription
      factor Zif268

<400> SEQUENCE: 8

Tyr Ala Cys Pro Val Glu Ser Cys Asp Arg Arg Phe Ser Arg Ser Asp
 1               5                  10                  15

Glu Leu Thr Arg His Ile Arg Ile His Thr Gly Gln Lys Pro Phe Gln
                20                  25                  30

Cys Arg Ile Cys Met Arg Asn Phe Ser Arg Ser Asp His Leu Thr Thr
            35                  40                  45

His Ile Arg Thr His Thr Gly Glu Lys Pro Phe Ala Cys Asp Ile Cys
        50                  55                  60

Gly Arg Lys Phe Ala Arg Ser Asp Glu Arg Lys Arg His Thr Lys Ile
 65                 70                  75                  80

His Leu Arg Gln Lys
                85

<210> SEQ ID NO 9
```

```
<211> LENGTH: 94
<212> TYPE: PRT
<213> ORGANISM: Artificial Sequence
<220> FEATURE:
<223> OTHER INFORMATION: Description of Artificial Sequence:amino acids
      531-624 in Sp-1 transcription factor

<400> SEQUENCE: 9

Pro Gly Lys Lys Lys Gln His Ile Cys His Ile Gln Gly Cys Gly Lys
 1               5                  10                  15

Val Tyr Gly Lys Thr Ser His Leu Arg Ala His Leu Arg Trp His Thr
            20                  25                  30

Gly Glu Arg Pro Phe Met Cys Thr Trp Ser Tyr Cys Gly Lys Arg Phe
        35                  40                  45

Thr Arg Ser Asp Glu Leu Gln Arg His Lys Arg Thr His Thr Gly Glu
    50                  55                  60

Lys Lys Phe Ala Cys Pro Glu Cys Pro Lys Arg Phe Met Arg Ser Asp
65                  70                  75                  80

His Leu Ser Lys His Ile Lys Thr His Gln Asn Lys Lys Gly
                85                  90

<210> SEQ ID NO 10
<211> LENGTH: 98
<212> TYPE: PRT
<213> ORGANISM: Artificial Sequence
<220> FEATURE:
<223> OTHER INFORMATION: Description of Artificial Sequence:Sp-1
      transcription factor consensus sequence

<400> SEQUENCE: 10

Met Glu Lys Leu Arg Asn Gly Ser Gly Asp Pro Gly Lys Lys Lys Gln
 1               5                  10                  15

His Ala Cys Pro Glu Cys Gly Lys Ser Phe Ser Lys Ser Ser His Leu
            20                  25                  30

Arg Ala His Gln Arg Thr His Thr Gly Glu Arg Pro Tyr Lys Cys Pro
        35                  40                  45

Glu Cys Gly Lys Ser Phe Ser Arg Ser Asp Glu Leu Gln Arg His Gln
    50                  55                  60

Arg Thr His Thr Gly Glu Lys Pro Tyr Lys Cys Pro Glu Cys Gly Lys
65                  70                  75                  80

Ser Phe Ser Arg Ser Asp His Leu Ser Lys His Gln Arg Thr His Gln
                85                  90                  95

Asn Lys

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:natural
      Zif268 binding site

<400> SEQUENCE: 11
gcgtgggcgc                                                          10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence:target site
      containing three D-able subsites
```

```
<220> FEATURE:
<221> NAME/KEY: misc_feature
<222> LOCATION: (1)...(10)
<223> OTHER INFORMATION: n is a, c, g, or t

<400> SEQUENCE: 12 ggntgnggnn                                                                 10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence:target site
      with two overlapping D-able subsites
<220> FEATURE:
<221> NAME/KEY: misc_feature
<222> LOCATION: (1)...(10)
<223> OTHER INFORMATION: n is a, c, g, or t

<400> SEQUENCE: 13 nngkngknnn                                                                 10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence:target site
      with three overlapping D-able subsites
<220> FEATURE:
<221> NAME/KEY: misc_feature
<222> LOCATION: (1)...(10)
<223> OTHER INFORMATION: n is a, c, g, or t

<400> SEQUENCE: 14 nngkngkngk                                                                 10

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)...(22)
<223> OTHER INFORMATION: n is g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 15
gnggnngnnn nngnggnngn nn                                                   22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
```

<223> OTHER INFORMATION: n = g, a, c or t, may be present or absent

<400> SEQUENCE: 16
gnggnngnnn nnngnggnng nnn                         23

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 17
gnggnngnnn nngnngnggn nn                          22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 18
gnggnngnnn nnngnngngg nnn                         23

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 19
gnggnngnnn nngnggnngn gg                          22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base

```
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 20
gnggnngnnn nnngnggnng ngg                                              23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 21
gnngnggnnn nngnggnngn nn                                               22

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 22
gnngnggnnn nnngnggnng nnn                                              23

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 23
gnngnggnnn nngnngnggn nn                                               22

<210> SEQ ID NO 24
<211> LENGTH: 23
<212> TYPE: DNA
<213> ORGANISM: Artificial Sequence
```

```
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 24
gnngnggnnn nnngnngngg nnn                                    23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 25
gnngnggnnn nngnggnngn gg                                     22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 26
gnngnggnnn nnngnggnng ngg                                    23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 27
gnngnngngg nnngnggnng nnn                                    23
```

```
<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(24)
<223> OTHER INFORMATION: n = g, a, c or t
<220> FEATURE:
<221> NAME/KEY: modified_base
<222> LOCATION: (12)..(14)
<223> OTHER INFORMATION: n = g, a, c or t, may be present or absent

<400> SEQUENCE: 28
gnngnngngg nnnngnggnn gnnn                                          24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 29
gnngnngngg nnngnngngg nnn                                           23

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(24)
<223> OTHER INFORMATION: n = g, a, c or t
<220> FEATURE:
<221> NAME/KEY: modified_base
<222> LOCATION: (12)..(14)
<223> OTHER INFORMATION: n = g, a, c or t, may be present or absent

<400> SEQUENCE: 30
gnngnngngg nnnngnngng gnnn                                          24

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent
```

```
<400> SEQUENCE: 31
gnngnngngg nnngnggnng ngg                                          23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(24)
<223> OTHER INFORMATION: n = g, a, c or t
<220> FEATURE:
<221> NAME/KEY: modified_base
<222> LOCATION: (12)..(14)
<223> OTHER INFORMATION: n = g, a, c or t, may be present or absent

<400> SEQUENCE: 32
gnngnngngg nnnngnggnn gngg                                         24

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(19)
<223> OTHER INFORMATION: n = g, a, c or t

<400> SEQUENCE: 33
gnngnngngg nggnngnnn                                               19

<210> SEQ ID NO 34
      LENGTH:    19
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(19)
<223> OTHER INFORMATION: n = g, a, c or t

<400> SEQUENCE: 34
gnngnngngg nngnggnnn                                               19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 1
<220> FEATURE:
<221> NAME/KEY: modified_base
<222> LOCATION: (1)..(19)
<223> OTHER INFORMATION: n = g, a, c or t

<400> SEQUENCE: 35
gnngnngngg nngnngngg                                               19

<210> SEQ ID NO 36
```

```
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 36
knggnnknnn nnknggnnkn nn                                              22

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 37
knggnnknnn nnnknggnnk nnn                                             23

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 38
knggnnknnn nnknnknggn nn                                              22

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 39
```

```
knggnnknnn nnnknnkngg nnn                                              23
```

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 40

```
knggnnknnn nnknnknnkn gg                                               22
```

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 41

```
knggnnknnn nnnknnknnk ngg                                              23
```

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 42

```
knnknggnnn nnknggnnkn nn                                               22
```

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:

<221> NAME/KEY: modified_base
<222> LOCATION: (11)..(13)
<223> OTHER INFORMATION: n = g, a, c or t, may be present or absent

<400> SEQUENCE: 43
knnknggnnn nnnknggnnk nnn                                             23

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 44
knnknggnnn nnknnknggn nn                                              22

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 45
knnknggnnn nnnknnkngg nnn                                             23

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 46
knnknggnnn nnknnknnkn gg                                              22

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2

```
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 47
knnknggnnn nnnknnknnk ngg                                           23

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (11)..(12)
<223> OTHER INFORMATION: n = g, a, c or t, may be present or absent

<400> SEQUENCE: 48
knnknnkngg nnknggnnkn nn                                            22

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (12)..(13)
<223> OTHER INFORMATION: n = g, a, c or t, may be present or absent

<400> SEQUENCE: 49
knnknnkngg nnnknggnnk nnn                                           23

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (11)..(12)
<223> OTHER INFORMATION: n = g, a, c or t, may be present or absent

<400> SEQUENCE: 50
knnknnkngg nnknnknggn nn                                            22

<210> SEQ ID NO 51
<211> LENGTH: 23
```

```
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (12)..(13)
<223> OTHER INFORMATION: n = g, a, c or t, may be present or absent

<400> SEQUENCE: 51
knnknnkngg nnnknnkngg nnn                                            23

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (11)..(12)
<223> OTHER INFORMATION: n = g, a, c or t, may be present or absent

<400> SEQUENCE: 52
knnknnkngg nnnknnknnkn gg                                            22

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (12)..(13)
<223> OTHER INFORMATION: n = g, a, c or t, may be present or absent

<400> SEQUENCE: 53
knnknnkngg nnnknnknnk ngg                                            23

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(19)
<223> OTHER INFORMATION: n = g, a, c or t

<400> SEQUENCE: 54
knnknnkngg nggnnknnn                                                 19

<210> SEQ ID NO 55
```

-continued

```
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(19)
<223> OTHER INFORMATION: n = g, a, c or t

<400> SEQUENCE: 55
knnknnkngg nnknggnnn                                             19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 2
<220> FEATURE:
<221> NAME/KEY: modified_base
<222> LOCATION: (1)..(19)
<223> OTHER INFORMATION: n = g, a, c or t

<400> SEQUENCE: 56
knnknnkngg nnknnkngg                                             19

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 57
kngknnknnn nnkngknnkn nn                                         22

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 58
kngknnknnn nnkngknnk nnn                                         23

<210> SEQ ID NO 59
<211> LENGTH: 22
<212> TYPE: DNA
<213> ORGANISM: Artificial Sequence
```

```
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 59
kngknnknnn nnknnkngkn nn                                              22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 60
kngknnknnn nnnknnkngk nnn                                             23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 61
kngknnknnn nnknnknnkn gk                                              22

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 62
kngknnknnn nnnknnknnk ngk                                             23
```

```
<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 63
knnkngknnn nnkngknnkn nn                                              22

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 64
knnkngknnn nnnkngknnk nnn                                             23

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 65
knnkngknnn nnknnkngkn nn                                              22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent
```

<400> SEQUENCE: 66
knnkngknnn nnnknnkngk nnn                                          23

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (10)..(12)
<223> OTHER INFORMATION: n = g, a, c or t, may be present or absent

<400> SEQUENCE: 67
knnkngknnn nnknnknnkn gk                                           22

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (11)..(13)
<223> OTHER INFORMATION: n = g, a, c or t, may be present or absent

<400> SEQUENCE: 68
knnkngknnn nnnknnknnk ngk                                          23

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (11)..(12)
<223> OTHER INFORMATION: n = g, a, c or t, may be present or absent

<400> SEQUENCE: 69
knnknnkngk nnkngknnkn nn                                           22

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)

<223> OTHER INFORMATION: n = g, a, c or t
<220> FEATURE:
<221> NAME/KEY: modified_base
<222> LOCATION: (12)..(13)
<223> OTHER INFORMATION: n = g, a, c or t, may be present or absent

<400> SEQUENCE: 70
knnknnkngk nnnkngknnk nnn                                        23

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (11)..(12)
<223> OTHER INFORMATION: n = g, a, c or t, may be present or absent

<400> SEQUENCE: 71
knnknnkngk nnknnkngkn nn                                         22

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (12)..(13)
<223> OTHER INFORMATION: n = g, a, c or t, may be present or absent

<400> SEQUENCE: 72
knnknnkngk nnnknnkngk nnn                                        23

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(22)
<223> OTHER INFORMATION: n = g, a, c or t
<220> FEATURE:
<221> NAME/KEY: modified_base
<222> LOCATION: (11)..(12)
<223> OTHER INFORMATION: n = g, a, c or t, may be present or absent

<400> SEQUENCE: 73
knnknnkngk nnknnknnkn gk                                         22

<210> SEQ ID NO 74
<211> LENGTH: 23
<212> TYPE: DNA
<213> ORGANISM: Artificial Sequence
<220> FEATURE:

```
<223> OTHER INFORMATION: Description of Artificial Sequence:target site
      DNA motif searched by protocol 3
<220> FEATURE:
<221> NAME/KEY: modified_base
<222> LOCATION: (1)..(23)
<223> OTHER INFORMATION: n = g, a, c or t
<220> FEATURE:
<221> NAME/KEY: modified_base
<222> LOCATION: (12)..(13)
<223> OTHER INFORMATION: n = g, a, c or t, may be present or absent

<400> SEQUENCE: 74
knnknnkngk nnnknnknnk ngk                                           23

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(19)
<223> OTHER INFORMATION: n = g, a, c or t

<400> SEQUENCE: 75
knnknnkngk ngknnknnn                                                19

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(19)
<223> OTHER INFORMATION: n = g, a, c or t

<400> SEQUENCE: 76
knnknnkngk nnkngknnn                                                19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence:target site
      DNA motif searched by protocol 3
<220> FEATURE:
<221> NAME/KEY: modified_base
<222> LOCATION: (1)..(19)
<223> OTHER INFORMATION: n = g, a, c or t

<400> SEQUENCE: 77
knnknnkngk nnknnkngk                                                19

<210> SEQ ID NO 78
<211> LENGTH: 10
<212> TYPE: DNA
<213> ORGANISM: Glycine max
<220> FEATURE:
<223> OTHER INFORMATION: soybean FAD2-1 cDNA ZFP target segment FAD 1

<400> SEQUENCE: 78
gaggtagagg                                                          10
```

-continued

<210> SEQ ID NO 79
<211> LENGTH: 10
<212> TYPE: DNA
<213> ORGANISM: Glycine max
<220> FEATURE:
<223> OTHER INFORMATION: soybean FAD2-1 cDNA target segment FAD 2

<400> SEQUENCE: 79
gtcgtgtgga                                                          10

<210> SEQ ID NO 80
<211> LENGTH: 10
<212> TYPE: DNA
<213> ORGANISM: Glycine max
<220> FEATURE:
<223> OTHER INFORMATION: soybean FAD2-1 cDNA target segment FAD 3

<400> SEQUENCE: 80
gttgaggaag                                                          10

<210> SEQ ID NO 81
<211> LENGTH: 10
<212> TYPE: DNA
<213> ORGANISM: Glycine max
<220> FEATURE:
<223> OTHER INFORMATION: soybean FAD2-1 cDNA target segment FAD 4

<400> SEQUENCE: 81
gaggtggaag                                                          10

<210> SEQ ID NO 82
<211> LENGTH: 10
<212> TYPE: DNA
<213> ORGANISM: Glycine max
<220> FEATURE:
<223> OTHER INFORMATION: soybean FAD2-1 cDNA target segment FAD 5

<400> SEQUENCE: 82
taggtggtga                                                          10

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence:test
      sequence

<400> SEQUENCE: 83
agtgcgcggt gc                                                       12

<210> SEQ ID NO 84
<211> LENGTH: 10
<212> TYPE: DNA
<213> ORGANISM: Artificial Sequence
<220> FEATURE:
<223> OTHER INFORMATION: Description of Artificial Sequence:target site
      with base immediately to the 3' side of target site

<400> SEQUENCE: 84
agtgcgcggt                                                          10

<210> SEQ ID NO 85
<211> LENGTH: 10
<212> TYPE: DNA
<213> ORGANISM: Artificial Sequence
<220> FEATURE:

```
<223> OTHER INFORMATION: Description of Artificial Sequence:target site
      with base immediately to the 3' side of target
      site

<400> SEQUENCE: 85
gtgcgcggtg                                                              10

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence:target site
      with base immediately to the 3' side of target
      site

<400> SEQUENCE: 86
tgcgcggtgc                                                              10

<210> SEQ ID NO 87
<211> LENGTH: 10
<212> TYPE: DNA
<213> ORGANISM: Artificial Sequence
<220> FEATURE:
<223> OTHER INFORMATION: Description of Artificial Sequence:target site
      with base immediately to the 3' side of target site
<220> FEATURE:
<221> NAME/KEY: modified_base
<222> LOCATION: (10)
<223> OTHER INFORMATION: n = undefined

<400> SEQUENCE: 87 gcgcggtgcn                                                              10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence:finger F3
      for ordered output from optimal design target site

<400> SEQUENCE: 88

Glu Arg Asp His Leu Arg Thr
  1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence:finger F2
      for ordered output from optimal design target site

<400> SEQUENCE: 89

Arg Ser Asp Glu Leu Gln Arg
  1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence:finger F1
      for ordered output from optimal design target site

<400> SEQUENCE: 90

Arg Lys Asp Ser Leu Val Arg
```

```
<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence:finger for
      disordered output from optimal design target site

<400> SEQUENCE: 91

Arg Ser Asp Glu Leu Thr Arg
 1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence:finger for
      disordered output from optimal design target site

<400> SEQUENCE: 92

Arg Ser Asp Glu Arg Lys Arg
 1               5

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence:three finger
      ZFP design using F3, F2 and F1 fingers for ordered
      output from optimal design target site

<400> SEQUENCE: 93

Arg Lys Asp Ser Leu Val Arg Arg Ser Asp Glu Leu Gln Arg Glu Arg
 1               5                  10                  15

Asp His Leu Arg Thr
             20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence:ZFP sequence
      (F1, F2 and F3) from SBS design GR-223

<400> SEQUENCE: 94

Arg Ser Ala Asp Leu Thr Arg Arg Ser Asp His Leu Thr Arg Glu Arg
 1               5                  10                  15

Asp His Leu Arg Thr
             20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence:ZFP sequence
      (F1, F2 and F3) from Zif 268

<400> SEQUENCE: 95

Arg Ser Asp Glu Leu Thr Arg Arg Ser Asp His Leu Thr Thr Arg Ser
 1               5                  10                  15
```

```
Asp Glu Arg Lys Arg
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence:ZFP sequence
      (F1, F2, F3) from SP1

<400> SEQUENCE: 96

Lys Thr Ser His Leu Arg Ala Arg Ser Asp Glu Leu Gln Arg Arg Ser
  1               5                  10                  15

Asp His Leu Ser Lys
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence:ZFP sequence
      (F1, F2, F3) from SBS design GL-8.3.1

<400> SEQUENCE: 97

Arg Lys Asp Ser Leu Val Arg Thr Ser Asp His Leu Ala Ser Arg Ser
  1               5                  10                  15

Asp Asn Leu Thr Arg
            20
```

SELECTION OF SITES FOR TARGETING BY ZINC FINGER PROTEINS AND METHODS OF DESIGNING ZINC FINGER PROTEINS TO BIND TO PRESELECTED SITES

CROSS-REFERENCE TO RELATED APPLICATIONS

The present application is a divisional of U.S. application Ser. No. 09/229,007, filed Jan. 12, 1999 now U.S. Pat. No. 6,453,242, which is hereby incorporated by reference.

TECHNICAL FIELD

The invention resides in the technical fields of bioinformatics, and protein engineering.

BACKGROUND

Zinc finger proteins (ZFPs) are proteins that can bind to DNA in a sequence-specific manner. Zinc fingers were first identified in the transcription factor TFIIIA from the oocytes of the African clawed toad, *Xenopus laevis*. An exemplary motif characterizing one class of these protein ($C_2H_{12}$ class) is -Cys-$(X)_{2-4}$-Cys-$(X)_{12}$-His-$(X)_{3-5}$-His (SEQ ID NO:1) (where X is any amino acid). A single finger domain is about 30 amino acids in length, and several structural studies have demonstrated that it contains an alpha helix containing the two invariant histidine residues and two invariant cysteine residues in a beta turn co-ordinated through zinc. To date, over 10,000 zinc finger sequences have been identified in several thousand known or putative transcription factors. Zinc finger domains are involved not only in DNA-recognition, but also in RNA binding and in protein—protein binding. Current estimates are that this class of molecules will constitute about 2% of all human genes.

The x-ray crystal structure of Zif268, a three-finger domain from a murine transcription factor, has been solved in complex with a cognate DNA-sequence and shows that each finger can be superimposed on the next by a periodic rotation. The structure suggests that each finger interacts independently with DNA over 3 base-pair intervals, with side-chains at positions −1, 2, 3 and 6 on each recognition helix making contacts with their respective DNA triplet subsites. The amino terminus of Zif268 is situated at the 3' end of the DNA strand with which it makes most contacts. Recent results have indicated that some zinc fingers can bind to a fourth base in a target segment. If the strand with which a zinc finger protein makes most contacts is designated the target strand, some zinc finger proteins bind to a three base triplet in the target strand and a fourth base on the nontarget strand. The fourth base is complementary to the base immediately 3' of the three base subsite.

The structure of the Zif268-DNA complex also suggested that the DNA sequence specificity of a zinc finger protein might be altered by making amino acid substitutions at the four helix positions (−1, 2, 3 and 6) on each of the zinc finger recognition helices. Phage display experiments using zinc finger combinatorial libraries to test this observation were published in a series of papers in 1994 (Rebar et al., *Science* 263, 671–673 (1994); Jamieson et al., *Biochemistry* 33, 5689–5695 (1994); Choo et al, *PNAS* 91, 11163–11167 (1994)). Combinatorial libraries were constructed with ran- domized side-chains in either the first or middle finger of Zif268 and then used to select for an altered Zif268 binding site in which the appropriate DNA sub-site was replaced by an altered DNA triplet. Further, correlation between the nature of introduced mutations and the resulting alteration in binding specificity gave rise to a partial set of substitution rules for design of ZFPs with altered binding specificity.

Greisman & Pabo, *Science* 275, 657–661 (1997) discuss an elaboration of the phage display method in which each finger of a Zif268 was successively randomized and selected for binding to a new triplet sequence. This paper reported selection of ZFPs for a nuclear hormone response element, a p53 target site and a TATA box sequence.

A number of papers have reported attempts to produce ZFPs to modulate particular target sites. For example, Choo et al., *Nature* 372, 645 (1994), report an attempt to design a ZFP that would repress expression of a brc-abl oncogene. The target segment to which the ZFPs would bind was a nine base sequence 5'GCA GAA GCC3' chosen to overlap the junction created by a specific oncogenic translocation fusing the genes encoding brc and abl. The intention was that a ZFP specific to this target site would bind to the oncogene without binding to abl or brc component genes. The authors used phage display to screen a mini-library of variant ZFPs for binding to this target segment. A variant ZFP thus isolated was then reported to repress expression of a stably transfected brc-able construct in a cell line.

Pomerantz et al., *Science* 267, 93–96 (1995) reported an attempt to design a novel DNA binding protein by fusing two fingers from Zif268 with a homeodomain from Oct-1. The hybrid protein was then fused with a transcriptional activator for expression as a chimeric protein. The chimeric protein was reported to bind a target site representing a hybrid of the subsites of its two components. The authors then constructed a reporter vector containing a luciferase gene operably linked to a promoter and a hybrid site for the chimeric DNA binding protein in proximity to the promoter. The authors reported that their chimeric DNA binding protein could activate expression of the luciferase gene.

Liu et al., *PNAS* 94, 5525–5530 (1997) report forming a composite zinc finger protein by using a peptide spacer to link two component zinc finger proteins each having three fingers. The composite protein was then further linked to transcriptional activation domain. It was reported that the resulting chimeric protein bound to a target site formed from the target segments bound by the two component zinc finger proteins. It was further reported that the chimeric zinc finger protein could activate transcription of a reporter gene when its target site was inserted into a reporter plasmid in proximity to a promoter operably linked to the reporter.

Choo et al., WO 98/53058, WO98/53059, and WO 98/53060 (1998) discuss selection of zinc finger proteins to bind to a target site within the HIV Tat gene. Choo et al. also discuss selection of a zinc finger protein to bind to a target site encompassing a site of a common mutation in the oncogene ras. The target site within ras was thus constrained by the position of the mutation.

None of the above studies provided criteria for systematically evaluating the respective merits of the different potential target sites within a candidate gene. The phage display studies by Rebar et al., supra, Jamieson et al., supra and Choo et al, *PNAS*. (1994) supra, all focused on alterations of the natural Zif268 binding-site, 5'GCG TGG GCGc3' (SEQ ID NO:11), and were not made with reference to a predetermined target gene. Choo et al. *Nature* (1994), supra's selection of target site was constrained solely by the intent that the site overlap the interface between brc and abl segments and did not involve a comparison of different potential target sites. Likewise, Greisman & Pabo chose certain target sites because of their known regulatory roles and did not consider the relative merits of different potential target segments within a preselected target gene. Similarly, Choo et al. (1998), supra's choice of target site within ras was constrained by the position of a mutation. No criterion is provided for Choo et al. (1998)'s selection of a target site in HIV Tat. Finally, both Pomerantz et al., supra and Liu et al., supra constructed artificial hybrid target sites for composite zinc fingers and then inserted the target sites into reporter constructs.

SUMMARY OF THE INVENTION

The invention provides methods of selecting a target site within a target sequence for targeting by a zinc finger protein. Some such methods comprise providing a target nucleic acid to be targeted by a zinc finger protein and outputting a target site within the target nucleic acid comprising 5'NNx aNy bNzc3'. Each of (x, a), (y, b) and (z, c) is (N, N) or (G, K) provided at least one of (x, a), (y, b) and (z, c) is (G, K). N and K are IUPAC-IUB ambiguity codes. In some methods, a plurality of segments within the target nucleic acid are selected and a subset of the plurality of segments comprising 5'NNx aNy bNzc3' is output. Typically the target nucleic acid comprises a target gene. In some methods, at least two of (x, a), (y, b) and (z, c) is (G, K) In some methods, all three of (x, a), (y, b) and (z, c) are (G, K). Some methods further comprise identifying a second segment of the gene comprising 5'NNx aNy bNzc3', wherein each of (x, a), (y, b) and (z, c) is (N, N) or (G, K); at least one of (x, a), (y, b) and (z, c) is (G, K). and N and K are IUPAC-IUB ambiguity codes. In some methods, in the second segment at least two of (x, a), (y, b) and (z, c) are (G, K). In some methods, all three of at least one of (x, a), (y, b) and (z, c) are (G, K). In some methods, the first and second segments are separated by fewer than 5 bases in the target site.

Some methods further comprise synthesizing a zinc finger protein comprising first, second and third fingers that bind to the bNz aNy and NNx triplets respectively. In some such methods, the synthesizing step comprises synthesizing a first zinc finger protein comprising three zinc fingers that respectively bind to the NNx aNy and bNz triplets in the target segment and a second three fingers that respectively bind to the NNx aNy and bNz triplets in the second target segment. In some methods, each of the first, second and third fingers is selected or designed independently. In some methods, a finger is designed from a database containing designations of zinc finger proteins, subdesignations of finger components, and nucleic acid sequences bound by the zinc finger proteins. In some methods, a finger is selected by screening variants of a zinc finger binding protein for specific binding to the target site to identify a variant that binds to the target site.

Some methods further comprise contacting a sample containing the target nucleic acid with the zinc finger protein, whereby the zinc finger protein binds to the target site revealing the presence of the target nucleic acid or a particular allelic form thereof. In some methods, a sample containing the target nucleic acid is contacted with the zinc finger protein, whereby the zinc finger protein binds to the target site thereby modulating expression of the target nucleic acid.

In some methods, the target site occurs in a coding region. In some methods, the target site occurs within or proximal to a promoter, enhancer, or transcription start site. In some methods, the target site occurs outside a promoter, regulatory sequence or polymorphic site within the target nucleic acid.

In another aspect, the invention provides alternate methods for selecting a target site within a polynucleotide for targeting by a zinc finger protein. These methods, comprising providing a polynucleotide sequence and selecting a potential target site within the polynucleotide sequence; the potential target site comprising contiguous first, second and third triplets of bases at first, second and third positions in the potential target site. A plurality of subscores are then determined by applying a correspondence regime between triplets and triplet position in a sequence of three contiguous triplets, wherein each triplet has first, second and third corresponding positions, and each combination of triplet and triplet position has a particular subscore. A score is then calculated for the potential target site by combining subscores for the first, second, and third triplets. The selecting, determining and calculating steps are then repeated at least once on a further potential target site comprising first, second and third triplets at first, second and third positions of the further potential target site to determine a further score. Output is then provided of at least one potential target site with its score. In some methods, output is provided of the potential target site with the highest score. In some methods, output is provided of the n potential target sites with the highest scores, and the method further comprises providing user input of a value for n. In some methods, the subscores are combined by forming the product of the subscores. In some methods, the correspondence regime comprises 64 triplets, each having first, second, and third corresponding positions, and 192 subscores.

In some methods, the subscores in the correspondence regime are determined by assigning a first value as the subscore of a subset of triplets and corresponding positions, for each of which there is an existing zinc finger protein that comprising a finger that specifically binds to the triplet from the same position in the existing zinc finger protein as the corresponding position of the triplet in the correspondence regime; assigning a second value as the subscore of a subset of triplets and corresponding positions, for each of which there is an existing zinc finger protein that comprises a finger that specifically binds to the triplet from a different position in the existing zinc finger protein than the corresponding position of the triplet in the correspondence regime; and assigning a third value as the subscore of a subset of triplets and corresponding positions for which there is no existing zinc protein comprising a finger that specifically binds to the triplet.

In some methods, a context parameter with the subscore of at least one of the first, second and third triplets to give a scaled subscore of the at least one triplet. In some methods the context parameter is combined with the subscore when the target site comprises a base sequence 5'NNGK3', wherein NNG is the at least one triplet.

In another aspect, the invention provides methods of designing a zinc finger protein. Such methods use a database comprising designations for a plurality of zinc finger proteins, each protein comprising at least first, second and third fingers, and subdesignations for each of the three fingers of each of the zinc finger proteins; a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminal to C-terminal). A target site is provided for design of a zinc finger protein, the target site comprising continuous first, second and third triplets in a 3'–5' order. For the first, second and third triplet in the target site, first, second and third sets of zinc finger protein(s) in the database are identified, the first set comprising zinc finger protein(s) comprising a finger specifically binding to the first triplet in the target site, the second set comprising zinc finger protein(s) comprising a finger specifically binding to the second triplet in the target site, the third set comprising zinc finger protein(s) comprising a finger specifically binding to the third triplet in the target site. Designations and subdesignations of the zinc finger proteins in the first, second, and third sets identified in step (c) are then output. Some method further comprise producing a zinc finger protein that binds to the target site comprising a first finger from a zinc finger protein from the first set, a second finger from a zinc finger protein from the second set, and a third finger from a zinc finger protein from the third set Some methods further comprises identifying subsets of the first, second and third sets. The subset of the first set comprising zinc finger protein(s) comprising a finger that specifically binds to the first triplet in the target site from the first finger position of a zinc finger protein in the database. The subset of the second set comprising zinc finger protein(s) comprises a finger that specifically binds to the second triplet in the target site from the second finger position in a zinc finger protein in the database; the subset of the third set comprises a zinc finger protein(s) comprising a finger that specifically binds to the third triplet in the target site from a third finger position in a zinc finger protein in the database. Designations and subdesignations of the subset of the first, second and third sets are output. A zinc finger protein comprising a first finger from the first subset, a second finger from the second subset, and a third finger from the third subset is then produced. In some of the above methods of design, the target site is provided by user input. In some methods, the target site is provided by one of the target site selection methods described above.

The invention further provides computer program products for implementing any of the methods described above. One computer program product implements methods for selecting a target site within a polynucleotide for targeting by a zinc finger protein. Such a product comprises (a) code for providing a polynucleotide sequence; (b) code for selecting a potential target site within the polynucleotide sequence; the potential target site comprising first, second and third triplets of bases at first, second and third positions in the potential target site; (c) code for calculating a score for the potential target site from a combination of subscores for the first, second, and third triplets, the subscores being obtained from a correspondence regime between triplets and triplet position, wherein each triplet has first, second and third corresponding positions, and each corresponding triplet and position has a particular subscore; (d) code for repeating steps (b) and (c) at least once on a further potential target site comprising first, second and third triplets at first, second and third positions of the further potential target site to determine a further score; e) code for providing output of at least one of the potential target site with its score; and (f) a computer readable storage medium for holding the codes.

The invention further provides computer systems for implementing any of the methods described above. One such system for selecting a target site within a polynucleotide for targeting by a zinc finger protein, comprises (a) a memory; (b) a system bus; and (c) a processor. The processor is operatively disposed to: (1) provide or receive a polynucleotide sequence; (2) select a potential target site within the polynucleotide sequence; the potential target site comprising first, second and third triplets of bases at first, second and third positions in the potential target site; (3) calculate a score for the potential target site from a combination of subscores for the first, second, and third triplets, the subscores being obtained from a correspondence regime between triplets and triplet position, wherein each triplet has first, second and third corresponding positions, and each corresponding triplet and position has a particular subscore; (4) repeat steps (2) and (3) at least once on a further potential target site comprising first, second and third triplets at first, second and third positions of the further potential target site to determine a further score; (5) provide output of at least one of the potential target site with its score A further computer program product for producing a zinc finger protein comprises: (a) code for providing a database comprising designations for a plurality of zinc finger proteins, each protein comprising at least first, second and third fingers; subdesignations for each of the three fingers of each of the zinc finger proteins; a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminus to C-terminus); (b) code for providing a target site for design of a zinc finger protein, the target site comprising at least first, second and third triplets; (c) for the first, second and third triplet in the target site, code for identifying first, second and third sets of zinc finger protein(s) in the database, the first set comprising zinc finger protein(s) comprising a finger specifically binding to the first triplet in the target site, the second set comprising a finger specifically binding to the second triplet in the target site, the third set comprising a finger specifically binding to the third triplet in the target site; (d) code for outputting designations and subdesignations of the zinc finger proteins in the first, second, and third sets identified in step (c) and, (e) a compute readable storage medium for holding the codes.

The invention further provides a system for producing a zinc finger protein. The system comprises (a) a memory; (b) a system bus; and (c) a processor. The processor is operatively disposed to: (1) provide a database comprising designations for a plurality of zinc finger proteins, each protein comprising at least first, second and third fingers, subdesignations for each of the three fingers of each of the zinc finger proteins; a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminus to C-terminus); (2) provide a target site for design of a zinc finger protein, the target site comprising at least first, second and third triplets, (3) for the first, second and third triplet in the target site, identify first, second and third sets of zinc finger protein(s) in the database, the first set comprising zinc finger protein(s) comprising a finger specifically binding to the first triplet in the target site, the second set comprising a finger specifically binding to the second triplet in the target site, the third set comprising a finger specifically binding to the third triplet in the target site; and (4) output designations and subdesignations of the zinc finger proteins in the first, second, and third sets identified in step (3).

Definitions

Figure 1:
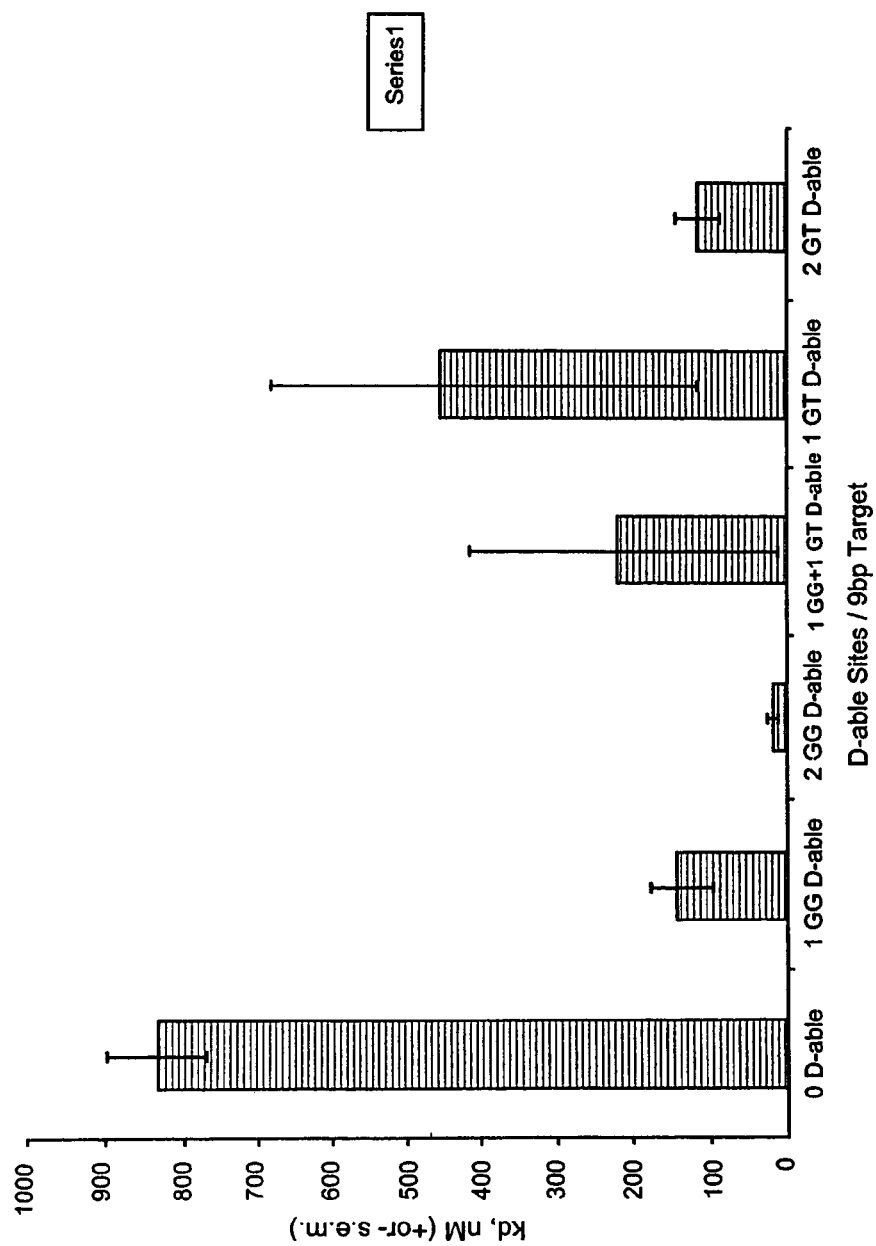
FIG. 1 shows a chart providing data that the presence and number of sub sites in a target site bound by a zinc finger protein correlates with binding affinity.

A zinc finger DNA binding protein is a protein or segment within a larger protein that binds DNA in a sequence-specific manner as a result of stabilization of protein structure through cordination on of zinc ion. The term zinc finger DNA binding protein is often abbreviated as zinc finger protein or ZFP.

A designed zinc finger protein is a protein not occurring in nature whose design/composition results principally from rational criteria. Rational criteria for design include application of substitution rules and computerized algorithms for processing information in a database storing information of existing ZFP designs and binding data. A selected zinc finger protein is a protein not found in nature whose production results primarily from an empirical process such as phage display.

The term naturally-occurring is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

A nucleic acid is operably linked when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by up to several kilobases or more and intronic sequences may be of variable lengths, some polynucleotide elements may be operably linked but not contiguous.

A specific binding affinity between, for example, a ZFP and a specific target site means a binding affinity of at least $1 \times 10^6$ $M^{-1}$.

The terms "modulating expression" "inhibiting expression" and "activating expression" of a gene refer to the ability of a zinc finger protein to activate or inhibit transcription of a gene. Activation includes prevention of subsequent transcriptional inhibition (i.e., prevention of repression of gene expression) and inhibition includes prevention of subsequent transcriptional activation (i.e., prevention of gene activation). Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, beta-galactosidase, GFP (see, e.g., Mistili & Spector, *Nature Biotechnology* 15:961–964 (1997)); changes in signal transduction, phosphorylation and dephosphorylation, receptor-ligand interactions, second messenger concentrations (e.g., cGMP, cAMP, IP3, and Ca2+), cell growth, neovascularization, in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

A "regulatory domain" refers to a protein or a protein subsequence that has transcriptional modulation activity. Typically, a regulatory domain is covalently or non-covalently linked to a ZFP to modulate transcription. Alternatively, a ZFP can act alone, without a regulatory domain, or with multiple regulatory domains to modulate transcription.

A D-able subsite within a target site has the motif 5'NNGK3'. A target site containing one or more such motifs is sometimes described as a D-able target site. A zinc finger appropriately designed to bind to a D-able subsite is sometimes referred to as a D-able finger. Likewise a zinc finger protein containing at least one finger designed or selected to bind to a target site including at least one D-able subsite is sometimes referred to as a D-able zinc finger protein.

DETAILED DESCRIPTION

I. General

In one aspect, the invention is directed to methods of selecting appropriate segments within a preselected target gene for design of a zinc finger protein intended for use in modulating or detecting the gene. The size of a potential target gene can vary widely from around 100 to several 100,000 bp. A zinc finger protein can bind to a small subsequence or target site within such gene. For example, zinc finger proteins containing three fingers typically bind to nine or ten bases of a target gene. The invention provides criteria and methods for selecting optimum subsequence(s) from a target gene for targeting by a zinc finger protein.

Some of the methods of target site selection seek to identify one or more target segments having a DNA motif containing one or more so-called D-able subsites. A D-able subsite is defined by a characteristic DNA sequence formula as discussed in detail below. A zinc finger protein is able to bind such a motif in a manner such that at least one component finger of the zinc finger protein contacts an additional base outside the three base subsite usually bound by a finger. If two D-able sites are present in the target segment, then two component fingers of a zinc finger protein can each bind to four bases of the target site. If three D-able subsites are present in the target segment, then three component fingers of zinc finger protein can each bind to four bases in the target site. In general zinc finger proteins binding to target sites containing at least one D-able subsite show higher binding affinity than zinc finger proteins that bind to target segments lacking a D-able subsite. Likewise, zinc finger proteins binding to a target site with two D-able subsites generally show higher binding affinity than zinc finger proteins that bind to a target site with one D-able subsite, and zinc finger proteins with three D-able subsites generally show higher binding affinity than zinc finger proteins that bind to a target site with two D-able subsites. Although an understanding of mechanism is not required for practice of the invention, it is believed that the higher binding affinity results from the additional interactions possible between a zinc finger and four bases in a target segment relative to the interactions possible between a zinc finger and three bases in a target segment. In general, the potential for high affinity binding of target segments with D-able subsites makes them the target sites of choice from within target genes for design of zinc finger proteins because higher binding affinity often results in a greater extent of, and/or greater specificity in, modulation of a target gene.

Other methods of the invention are directed to selection of target segments within target genes by additional or alternative criteria to the D-able subsite. The principal criteria for selection of target segments in such methods are provided in the form of a correspondence regime between different triplets of three bases and the three possible positions of a triplet within a nine-base site (i.e., bases 1–3, 4–6 and 7–9). An exemplary correspondence regime is shown in Table 1. The correspondence regime provides different values for different combinations of triplet and triplet position within a target site. A potential target site within a target gene is evaluated by determining a score for the site by combining subscores for its component triplets obtained from the correspondence regime. The scores of different potential target sites are compared, with a high score indicating desirability of a particular segment as a target site for design of zinc finger binding protein.

In another aspect, the invention provides methods of designing zinc finger proteins that bind to a preselected target site. These methods can, of course, be used following the preselection of target sites according to the procedures and criteria described above. The methods of design use a database containing information about previously characterized zinc finger proteins. This information includes names or other designations of previously characterized zinc finger proteins, the amino acid sequence of their component fingers, and the nucleotide triplets bound by each finger of the proteins. Information in the database is accessed using an algorithm that allows one to select fingers from different previous designs for combination in a novel zinc finger protein having specificity for a chosen target site.

II. Zinc Finger Proteins

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein can bind to a subsite within the target site. The subsite includes a triplet of three contiguous bases all on the same strand (sometimes referred to as the target strand). The subsite may or may not also include a fourth base on the opposite strand that is the complement of the base immediately 3' of the three contiguous bases on the target strand. In many zinc finger proteins, a zinc finger binds to its triplet subsite substantially independently of other fingers in the same zinc finger protein. Accordingly, the binding specificity of zinc finger protein containing multiple fingers is usually approximately the aggregate of the specificities of its component fingers. For example, if a zinc finger protein is formed from first, second and third fingers that individually bind to triplets XXX, YYY, and ZZZ, the binding specificity of the zinc finger protein is 3'XXX YYY ZZZ5'.

The relative order of fingers in a zinc finger protein from N-terminal to C-terminal determines the relative order of triplets in the 3' to 5' direction in the target. For example, if a zinc finger protein comprises from N-terminal to C-terminal the first, second and third fingers mentioned above, then the zinc finger protein binds to the target segment 3'XXXYYYZZZ5'. If the zinc finger protein comprises the fingers in another order, for example, second finger, first finger, third finger, then the zinc finger protein binds to a target segment comprising a different permutation of triplets, in this example, 3'YYYXXXZZZ5' (see Berg & Shi, Science 271, 1081–1086 (1996)). The assessment of binding properties of a zinc finger protein as the aggregate of its component fingers is, however, only approximate, due to context-dependent interactions of multiple fingers binding in the same protein.

Two or more zinc finger proteins can be linked to have a target specificity that is the aggregate of that of the component zinc finger proteins (see e.g., Kim & Pabo, PNAS 95, 2812–2817 (1998)). For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 3'XXXYYYZZZ_AAABBBCCC5', where the underline indicates a short intervening region (typically 0–5 bases of any type). In this situation, the target site can be viewed as comprising two target segments separated by an intervening segment.

Linkage can be accomplished using any of the following peptide linkers. TGEKP (SEQ ID NO:2): (Liu et al., 1997, supra.); $(G_4S)_n$ (SEQ ID NO:3) (Kim et al., PNAS 93, 1156–1160 (1996.); GGRRGGGS (SEQ ID NO:4); LRQRDGERP (SEQ ID NO:5); LRQKDGGGSERP (SEQ ID NO:6); LRQKD$(G_3S)_2$ERP (SEQ ID NO:7). Alternatively, flexible linkers can be rationally designed using computer program capable of modeling both DNA-binding sites and the peptides themselves or by phage display methods. In a further variation, noncovalent linkage can be achieved by fusing two zinc finger proteins with domains promoting heterodimer formation of the two zinc finger proteins. For example, one zinc finger protein can be fused with fos and the other with jun (see Barbas et al., WO 95/119431).

Linkage of two zinc finger proteins is advantageous for conferring a unique binding specificity within a mammalian genome. A typical mammalian diploid genome consists of $3 \times 10^9$ bp. Assuming that the four nucleotides A, C, G, and T are randomly distributed, a given 9 bp sequence is present ~23,000 times. Thus a ZFP recognizing a 9 bp target with absolute specificity would have the potential to bind to ~23,000 sites within the genome. An 18 bp sequence is present once in $3.4 \times 10^{10}$ bp, or about once in a random DNA sequence whose complexity is ten times that of a mammalian genome.

A component finger of zinc finger protein typically contains about 30 amino acids and has the following motif (N—C) (SEQ ID NO:1):

| Cys-(X)$_{2-4}$-Cys-X.X.X.X.X.X.X.X.X.X.X-His-(X)$_{3-5}$-His |
|:---:|
| -1 1 2 3 4 5 6 7 |

The two invariant histidine residues and two invariant cysteine residues in a single beta turn are co-ordinated through zinc (see, e.g., Berg & Shi, Science 271, 1081–1085 (1996)). The above motif shows a numbering convention that is standard in the field for the region of a zinc finger conferring binding specificity. The amino acid on the left (N-terminal side) of the first invariant His residues is assigned the number +6, and other amino acids further to the left are assigned successively decreasing numbers. The alpha helix begins at residue 1 and extends to the residue following the second conserved histidine. The entire helix is therefore of variable length, between 11 and 13 residues.

The process of designing or selecting a nonnaturally occurring or variant ZFP typically starts with a natural ZFP as a source of framework residues. The process of design or selection serves to define nonconserved positions (i.e., positions −1 to +6) so as to confer a desired binding specificity. One suitable ZFP is the DNA binding domain of the mouse transcription factor Zif268. The DNA binding domain of this protein has the amino acid sequence:

```
(F1) YACPVESCDRRFSRSDELTRHIRIHTGQKP (F2) FQCRICMRNFSRSDHLTTHIRTHTGEKP (F3) FACDICGRKFARSDERKRHTKIHLRQK (SEQ ID NO:8)

and binds to a target 5' GCG TGG GCG 3'.
```

Another suitable natural zinc finger protein as a source of framework residues is Sp-1. The Sp-1 sequence used for construction of zinc finger proteins corresponds to amino acids 531 to 624 in the Sp-1 transcription factor. This sequence is 94 amino acids in length. The amino acid sequence of Sp-1 is as follows

```
PGKKKQHICHIQGCGKVYGKTSHLRAHLRWHTGERP

FMCTWSYCGKRFTRSDELQRHKRTHTGEKK

FACPECPKRFMRSDHLSKHIKTHQNKKG (SEQ ID NO:9)

Sp-1 binds to a target site 5'GGG GCG GGG3'.
```

An alternate form of Sp-1, an Sp-1 consensus sequence, has the following amino acid sequence:

meklrngsgd

```
PGKKKQHACPECGKSFSKSSHLRAHQRTHTGERP (SEQ ID NO:10)

YKCPECGKSFSRSDELQRHQRTHTGEKPYKCPEC

GKSFSRSDHLSKHQRTHQNKKG
```

(lower case letters are a leader sequence from Shi & Berg, *Chemistry and Biology* 1, 83–89. (1995). The optimal binding sequence for the Sp-1 consensus sequence is 5'GGGGCGGGG3'. Other suitable ZFPs are described below.

There are a number of substitution rules that assist rational design of some zinc finger proteins (see Desjarlais & Berg, *PNAS* 90, 2256–2260 (1993); Choo & Klug, PNAS 91, 11163–11167 (1994); Desjarlais & Berg, PNAS 89, 7345–7349 (1992); Jamieson et al., supra; Choo et al., WO 98/53057, WO 98/53058; WO 98/53059; WO 98/53060). Many of these rules are supported by site-directed mutagenesis of the three-finger domain of the ubiquitous transcription factor, Sp-1 (Desjarlais and Berg, 1992; 1993) One of these rules is that a 5' G in a DNA triplet can be bound by a zinc finger incorporating arginine at position 6 of the recognition helix. Another substitution rule is that a G in the middle of a subsite can be recognized by including a histidine residue at position 3 of a zinc finger. A further substitution rule is that asparagine can be incorporated to recognize A in the middle of triplet, aspartic acid, glutamic acid, serine or threonine can be incorporated to recognize C in the middle of triplet, and amino acids with small side chains such as alanine can be incorporated to recognize T in the middle of triplet A further substitution rule is that the 3' base of triplet subsite can be recognized by incorporating the following amino acids at position −1 of the recognition helix: arginine to recognize G, glutamine to recognize A, glutamic acid (or aspartic acid) to recognize C, and threonine to recognize T. Although these substitution rules are useful in designing zinc finger proteins they do not take into account all possible target sites. Furthermore, the assumption underlying the rules, namely that a particular amino acid in a zinc finger is responsible for binding to a particular base in a subsite is only approximate. Context-dependent interactions between proximate amino acids in a finger or binding of multiple amino acids to a single base or vice versa can cause variation of the binding specificities predicted by the existing substitution rules.

The technique of phage display provides a largely empirical means of generating zinc finger proteins with a desired target specificity (see e.g., Rebar, U.S. Pat. No. 5,789,538; Choo et al., WO 96/06166; Barbas et al., WO 95/19431 and WO 98/543111; Jamieson et al., supra). The method can be used in conjunction with, or as an alternative to rational design. The method involves the generation of diverse libraries of mutagenized zinc finger proteins, followed by the isolation of proteins with desired DNA-binding properties using affinity selection methods. To use this method, the experimenter typically proceeds as follows. First, a gene for a zinc finger protein is mutagenized to introduce diversity into regions important for binding specificity and/or affinity. In a typical application, this is accomplished via randomization of a single finger at positions −1, +2, +3, and +6, and sometimes accessory positions such as +1, +5, +8 and +10. Next, the mutagenized gene is cloned into a phage or phagemid vector as a fusion with gene III of a filamentous phage, which encodes the coat protein pIII. The zinc finger gene is inserted between segments of gene III encoding the membrane export signal peptide and the remainder of pIII, so that the zinc finger protein is expressed as an amino-terminal fusion with pIII or in the mature, processed protein. When using phagemid vectors, the mutagenized zinc finger gene may also be fused to a truncated version of gene III encoding, minimally, the C-terminal region required for assembly of pIII into the phage particle. The resultant vector library is transformed into *E. coli* and used to produce filamentous phage which express variant zinc finger proteins on their surface as fusions with the coat protein pIII. If a phagemid vector is used, then the this step requires superinfection with helper phage. The phage library is then incubated with target DNA site, and affinity selection methods are used to isolate phage which bind target with high affinity from bulk phage. Typically, the DNA target is immobilized on a solid support, which is then washed under conditions sufficient to remove all but the tightest binding phage. After washing, any phage remaining on the support are recovered via elution under conditions which disrupt zinc finger-DNA binding. Recovered phage are used to infect fresh *E. coli*, which is then amplified and used to produce a new batch of phage particles. Selection and amplification are then repeated as many times as is necessary to enrich the phage pool for tight binders such that these may be identified using sequencing and/or screening methods. Although the method is illustrated for pIII fusions, analogous principles can be used to screen ZFP variants as pVIII fusions.

Zinc finger proteins are often expressed with a heterologous domain as fusion proteins. Common domains for addition to the ZFP include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. A preferred domain for fusing with a ZFP when the ZFP is to be used for repressing expression of a target gene is the KRAB repression domain from the human KOX-1 protein (Thiesen et al., *New Biologist* 2, 363–374 (1990); Margolin et al., *Proc. Natl. Acad. Sci. USA* 91, 4509–4513 (1994); Pengue et al., *Nucl. Acids Res.* 22:2908–2914 (1994); Witzgall et al., *Proc. Natl. Acad. Sci. USA* 91, 4514–4518 (1994). Preferred domains for achieving activation include the HSV VP16 activation domain (see, e.g., Hagmann et al., *J. Virol.* 71, 5952–5962 (1997)) nuclear hormone receptors (see, e.g., Torchia et al., *Curr. Opin. Cell. Biol.* 10:373–383 (1998)); the p65 subunit of nuclear factor kappa B (Bitko & Barik, *J. Virol.* 72:5610–5618 (1998) and Doyle & Hunt, *Neuroreport* 8:2937–2942 (1997)); Liu et al., *Cancer Gene Ther.* 5:3–28 (1998)), or artificial chimeric functional domains such as VP64 (Seifpal et al., *EMBO J.* 11, 4961–4968 (1992)).

An important factor in the administration of polypeptide compounds, such as the ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629–634 (1996)). Another subsequence, the h (hydrophobic) domain of signal peptides, was found to have similar cell membrane translocation characteristics (see, e.g., Lin et al., *J. Biol. Chem.* 270: 14255–14258 (1995)).

Examples of peptide sequences which can be linked to a ZFP of the invention, for facilitating uptake of ZFP into cells, include, but are not limited to: an 11 amino acid peptide of the tat protein of HIV; a 20 residue peptide sequence which corresponds to amino acids 84–103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223–233 (1997)). Other suitable chemical moieties that provide enhanced cellular uptake may also be chemically linked to ZFPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334–3341 (1993); Perelle et al., *Infect. Immun.*, 61:5147–5156 (1993); Stenmark et al., *J. Cell Biol.* 113: 1025–1032 (1991); Donnelly et al., *PNAS* 90:3530–3534 (1993); Carbonetti et al., *Abstr. Annu. Meet. Am. Soc. Microbiol.* 95:295 (1995); Sebo et al., *Infect. Immun.* 63:3851–3857 (1995); Klimpel et al., *PNAS U.S.A.* 89:10277–10281 (1992); and Novak et al., *J. Biol. Chem.* 267:17186–17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

III. Selection of Target Gene

Zinc finger proteins can be used to modulate the expression of any target polynucleotide sequence. The sequence can be for example, genomic, cDNA or RNA or an expressed sequence tag (EST). Typically, the target polynucleotide includes a gene or a fragment thereof. The term gene is used broadly to include, for example, exonic regions, intronic regions, 5'UTRs, 3' UTRs, 5' flanking sequences, 3' flanking sequences, promoters, enhancers, transcription start sites, ribosome binding sites, regulatory sites, poly-adenylation sites. Target genes can be cellular, viral or from other sources including purely theoretical sequences. Target gene sequences can be obtained from databases, such as GenBank, the published literature or can be obtained de novo. Target genes include genes from pathological viruses and microorganisms for which repression of expression can be used to abort infection. Examples of pathogenic viruses include hepatitis (A, B, or C), herpes virus (e.g., VZV, HSV-1, HSV-6, HSV-II, and CMV, Epstein Barr virus), HIV, ebola, adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Some examples of pathogenic bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria.

Target genes also include genes from human or other mammals that contribute to disease. Some such genes are oncogenes, tumor suppressors or growth factors that contribute to cancer. Examples of oncogenes include hMSH2 (Fishel et al., *Cell* 75, 1027–1038 (1993)) and hMLH1 (Papadopoulos et al., *Science* 263, 1625–1628 (1994)). Some examples of growth factors include fibroblast growth factor, platelet-derived growth factor, GM-SCF, VEGF, EPO, Erb-B2, and hGH. Other human genes contribute to disease by rendering a subject susceptible to infection by a microorganism or virus. For example, certain alleles of the gene encoding the CCR5 receptor render a subject susceptible to infection by HIV. Other human genes, such as that encoding amyloid precursor protein or ApoE, contribute to other diseases, such as Alzheimer's disease. Target genes also include genes of human or other mammals that provide defense mechanisms against diseases due to other sources. For example, tumor repressor genes, provide protection against cancer. Expression of such genes is desirable and zinc finger proteins are used to activate expression.

Target genes also include genes that are normally turned off or expressed at low levels but which through activation can be used to substitute for another defective gene present in some individuals. For example, the fetal hemaglobin genes, which are normally inactive in adult humans, can be activated to substitute for the defective beta-globin gene in individuals with sickle cell anemia.

Target genes also include plant genes for which repression or activation leads to an improvement in plant characteristics, such as improved crop production, disease or herbicide resistance. For example, repression of expression of the FAD2–1 gene results in an advantageous increase in oleic acid and decrease in linoleic and linoleic acids.

IV. Design of Zinc Finger Proteins To Bind D-able Subsites

1. Methods

The invention provides methods that select a target gene, and identify a target site within the gene containing one to six (or more) D-able subsites. A zinc finger protein can then be synthesized that binds to the preselected site. These methods of target site selection are premised, in part, on the present inventors' recognition that the presence of one or more D-able subsites in a target segment confers the potential for higher binding affinity in a zinc finger protein selected or designed to bind to that site relative to zinc finger proteins that bind to target segments lacking D-able subsites. Experimental evidence supporting this insight is provided in Examples 2–9.

Figure 2:
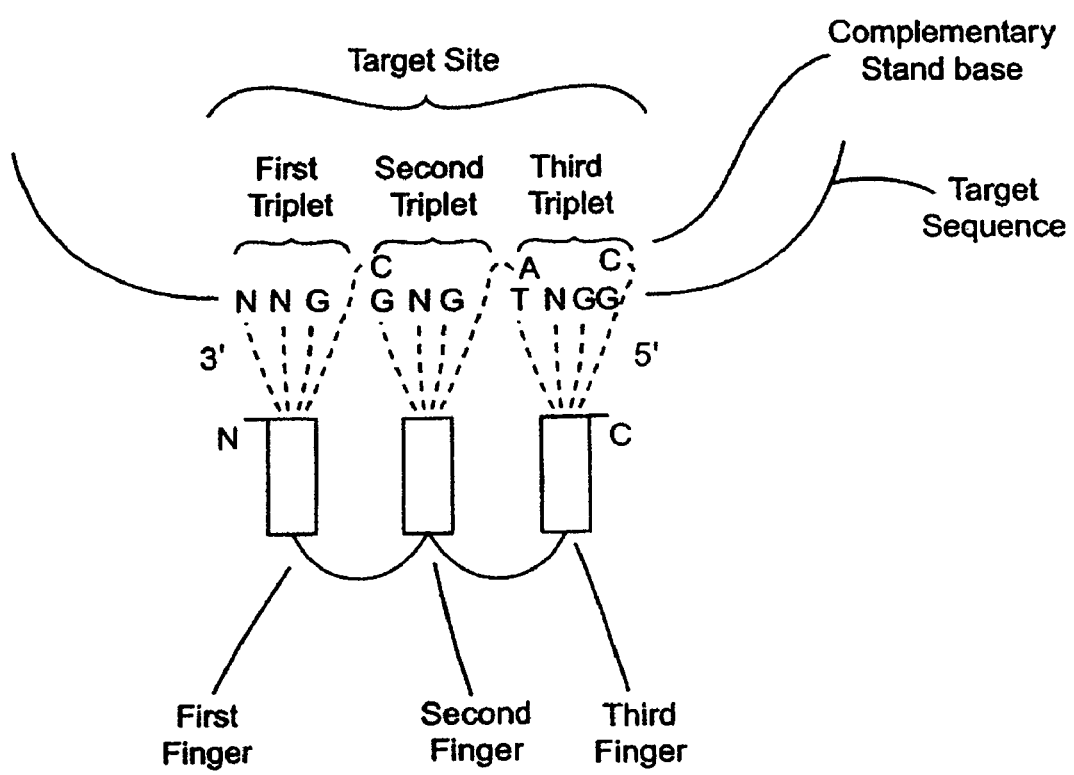
FIG. 2 shows a three finger zinc finger protein bound to a target site (SEQ ID NO:12) containing three D-able subsites.

A D-able subsite is a region of a target site that allows an appropriately designed single zinc finger to bind to up to four bases rather than up to three of the target site. Such a zinc finger binds to a triplet of bases on one strand of a double-stranded target segment (target strand) and a fourth base on the other strand (see FIG. 2) For a single zinc finger to bind a four base target segment imposes constraints both on the sequence of the target strand and on the amino acid sequence of the zinc finger. The target site within the target strand should include the "D-able" subsite motif 5'NNGK3', in which N and K are conventional IUPAC-IUB ambiguity codes. A zinc finger for binding to such a site should include an arginine residue at position −1 and an aspartic acid, (or less preferably a glutamic acid) at position +2. The arginine residue at position −1 interacts with the G residue in the D-able subsite. The aspartic acid (or glutamic acid) residue at position +2 of the zinc finger interacts with the opposite strand base complementary to the K base in the D-able subsite. It is the interaction between aspartic acid (symbol D) and the opposite strand base (fourth base) that confers the name D-able subsite. As is apparent from the D-able subsite formula, there are two subtypes of D-able subsites: 5'NNGG3' and 5'NNGT3'. For the former subsite, the aspartic acid or glutamic acid at position +2 of a zinc finger interacts with a C in the opposite strand to the D-able subsite. In the latter subsite, the aspartic acid or glutamic acid at position +2 of a zinc finger interacts with an A in the opposite strand to the D-able subsite. In general, NNGG is preferred over NNGT.

In the design of a zinc finger protein with three fingers, a target site should be selected in which at least one finger of the protein, and preferably, two or three fingers have the potential to bind a D-able subsite in a target site. Such can be achieved by selecting a target site from within a larger target gene having the formula 5'NNx aNy bNzc3', wherein wherein each of the sets (x, a), (y, b) and (z, c) is either (N, N) or (G, K);

at least one of (x, a), (y, b) and (z, c) is (G, K). and

N and K are IUPAC-IUB ambiguity codes.

In other words, at least one of the three sets (x, a), (y, b) and (z, c) is the set (G, K) meaning that the first position of the set is G and the second position is G or T. Those of the three sets (if any) which are not (G, K) are (N, N) meaning that the first position of the set can be occupied by any nucleotide and the second position of the set can be occupied by any nucleotide. As an example, the set (x, a) can be (G, K) and the sets (y, b) and (z, c) can both be (N, N).

In the formula 5'NNx aNy bNzc3', the triplets of NNx aNy and bNz represent the triplets of bases on the target strand bound by the three fingers in a zinc finger protein. The complements of the highlighted bases are the sites of potential fourth base binding on the nontarget strand. If only one of x, y and z is a G, and this G is followed by a K, the target site includes a single D-able subsite. For example, if only x is G and a is K, the site reads NNG KNy bNz w with the D-able subsite highlighted. If both x and y but not z are G and a and b are K, then the target site has two overlapping D-able subsites as follows: 5'NNG KNG KNz c3' (SEQ ID NO: 13) with one such site being represented in bold and the other in italics. If all three of x, y and z are G and a, b and c are K, then the target segment includes three D-able subsites, as follows 5'NNG KNG KNG K3' (SEQ ID NO:14), the D-able subsites being represented by bold, italics and underline.

The methods of the invention thus work by selecting a target gene, and systematically searching within the possible subsequences of the gene for target sites conforming to the formula 5'NNx aNy bNzc3', wherein wherein each of (x, a), (y, b) and (z, c) is (N, N) or (G, K);
at least one of (x, a), (y, b) and (z, c) is (G, K). and
N and K are IUPAC-IUB ambiguity codes.

In some such methods, every possible subsequence of 10 contiguous bases on either strand of a potential target gene is evaluated to determine whether it conforms to the above formula, and, if so, how many D-able subsites are present. Typically, such a comparison is performed by computer, and a list of target sites conforming to the formula are output. Optionally, such target sites can be output in different subsets according to how many D-able subsites are present.

In a variation, the methods of the invention identify first and second target segments, each independently conforming to the above formula. The two target segments in such methods are constrained to be adjacent or proximate (i.e., within about 0–5 bases) of each other in the target gene. The strategy underlying selection of proximate target segments is to allow the design of a zinc finger protein formed by linkage of two component zinc finger proteins specific for the first and second target segments respectively. These principles can be extended to select target sites to be bound by zinc finger proteins with any number of component fingers. For example, a suitable target site for a nine-finger protein would have three component segments, each conforming to the above formula.

The target sites identified by the above methods can be subject to further evaluation by other criteria or can be used directly for design or selection (if needed) and production of a zinc finger protein specific for such a site. A further criterion for evaluating potential target sites is proximity to particular regions within a gene. If a zinc finger protein is to be used to repress a cellular gene on its own (i.e., without linking the zinc finger protein to a repressing moiety), then the optimal location appears to be at the site of transcription initiation, or within about 50 bp upstream or downstream, or alternatively within an enhancer element to interfere with the formation of the transcription complex (Kim & Pabo, *J. Biol. Chem.* (1997) or compete for an essential enhancer binding protein. If, however, a ZFP is fused to a functional domain such as the KRAB repressor domain or the VP16 activator domain, the choice of location of the binding site is considerably more flexible and can be outside known regulatory regions. For example, a KRAB domain can repress transcription of a promoter up to at least 3-kb from where KRAB is bound. Thus, target sites can be selected that do not include or overlap segments of significance with target genes, such as regulatory sequences, or polymorphic sites. Other criteria for further evaluating target segments include the prior availability of zinc finger proteins binding to such segments or related segments, and/or ease of designing new zinc finger proteins to bind a given target segment. Implementation of such criteria in the selection process is discussed in further detail below.

Once a target segment has been selected, a zinc finger protein that binds to the segment can be provided by a variety of approaches. The simplest approach is to provide a precharacterized zinc finger protein from an existing collection that is already known to bind to the target site. However, in many instances, such a zinc finger protein does not exist. An alternative approach uses information in a database of existing zinc finger proteins and binding specificities to design new zinc finger proteins. This approach is described in more detail below. A further approach is to design a zinc finger protein based on substitution rules as discussed above. A still further alternative is to select a zinc finger protein with specificity for a given target by an empirical process such as phage display. In some such methods, each component finger of a zinc finger protein is designed or selected independently of other component fingers. For example, each finger can be obtained from a different pre-existing ZFP. or each finger can be subject to separate randomization and selection.

Once a zinc finger protein has been selected, designed, or otherwise provided to a given target segment, the zinc finger protein or the DNA encoding are synthesized. Exemplary methods for synthesizing and expressing DNA encoding zinc proteins are described below. The zinc finger protein or a polynucleotide encoding it can then be used for modulation of expression, or analysis of the target gene containing the target site to which the zinc finger protein binds.

2. D-able Zinc Finger Proteins

A zinc finger protein is described as D-able if it contains a finger that can bind to the fourth base of at least one D-able subsite, that is a polynucleotide sequence 5'NNGK3'. A preferred framework for designing D-able zinc fingers is the human wild type Sp-1 DNA binding domain. The target for the human transcription factor Sp-1 is 5'GGG GCG GGG3', and fingers 1 and 2 of this protein have an R-1 D+2 arrangement. Designed ZFPs can be identical to Sp-1 except in the recognition helix of each of the three fingers, where the sequences are designed to recognize each of the triplets with which they interact. The mouse ZFP Zif268, which binds the site GCG TGG GCG, is also suitable, having the R–1 D+2 arrangement in all three fingers.

Other zinc finger proteins as a source of framework residues for design of zinc finger proteins capable of binding to D-able subsites can be obtained from or derived from ZFPs from several alternative sources. For example, the TTK transcriptional regulatory protein of the fruit fly *Drosophila melanogaster* has been well characterized with regard to both the sequences of its recognition helices and its DNA site. The protein has only two fingers and binds to a six base target, so finger 2 interacts with the first DNA triplet and finger 1 recognizes the second triplet of the site. The site is 5'AAG GAT3' with a GG type D-able subsite present at the junction of the first and second triplet, and finger 2 has the R-1 D+2 sequence. Other suitable ZFPs are found in the unicellular eukaryote *Saccharomyces cerevisiae*. The ADR gene product is known to regulate expression of the ADH gene by binding within the ADH promoter. As described above for TTK, the ADR ZFP binding domain has two fingers, and binds to a six base target, TTGGAG. The finger 2 recognition helix has the R-1 D+2 sequence, appropriate for a ZFP binding to a target site with a D-able subsite.

IV. Selection of Target Sites by a Correspondence Regime

The invention further provides additional or alternative methods for selecting a target site from within a target gene. These methods are premised, in part, on the insights that different three-base subsites (triplets) bound by individual fingers have different desirabilities for zinc finger protein design, that these different desirabilities can be expressed as numerical values, and that the numerical values for the three individual triplets comprising a target site can be combined to give an overall score for the target site. The relative merits of different target sites can the be compared from their relative score.

The methods work by providing a polynucleotide sequence typically a gene or cDNA within which one wishes to select a target site for detection or modulation by a ZFP. In practice, one typically provides two sequences for the two strands of a polynucleotide sequence, but for simplicity, the method is illustrated for a single polynucleotide sequence. From within such a polynucleotide sequence, a potential target site of at least 9 bases comprising contiguous first, second and third triplets of bases is selected. The triplets are contiguous in that the first triplet occupies bases 7–9, the second triplet bases 4–6 and the third triplet bases 1–3 of a site, with base 1 in the 5'–3 orientation being designated base 1. This designation of triplets as first, second, and third is arbitrary and could be reversed. However, by designating the first triplet as occupying bases 7–9, the second triplet bases 4–6 and the third triplet bases 1–3, the first, second, and third fingers of a three finger ZFP in an N—C terminal orientation bind to the first, second and third triplets of a target site. Viewed in another manner, the first, second and third fingers in a zinc finger protein order from N terminal to C terminal are respectively specific for the first, second and third triplets in a target site ordered in the 3'–5' orientation.

A subscore is then determined for each triplet from a correspondence regime between triplets and corresponding positions within a target site. An exemplary correspondence regime is provided in Table 1. The correspondence regime is a matrix providing three values for each triplet at its three possible positions within a nine base target site. The table provides three values for each of the 64 possible triplets. For example, consider a potential target site 5'AAA AAG AAC3'. The AAC triplet occurs in the first position (bases 7–9) of the target site and is assigned a subscore of 1 from Table 1. The AAG triplet occurs in the second position of the target site (bases 4–6) and is assigned a subscore of 8. The AAA triplet occurs in the third position of the target site (bases 1–3) and is assigned a subscore of 8. The subscores of the three triplets in the potential target site are then combined, e.g., by multiplication or addition or some other function. For example, multiplication of the three triplet subscores gives a combined score of 1×8×8=64.

The process is then repeated for a second potential target site. Subscores are determined for each of the three component triplets of the second potential target site, and a combined score is calculated for the second potential target site. The process can then be repeated for further potential target sites. Optionally, the process can be repeated for every possible contiguous subsequence of at least 9 bases in either strand of a target gene of interest. When scores of all potential target sites of interest have been determined the scores are compared. In general a high score indicates desirability of a target site for design of a ZFP. One or more of the target sites identified with high scores can be outputted together with the score.

The designation of values in the correspondence regime can reflect any criteria that make one triplet subsite more desirable than another for zinc finger protein design or selection. The values in the exemplary correspondence regime of Table 1 reflect availability of previously characterized ZFPs known to bind a given nucleotide triplet. If for a given triplet in a given position of a target site, there exist one or more previously characterized ZFPs that specifically bind to a target segment including the triplet at the given position, then the combination of the triplet and given position is assigned a score of 10. If for a given triplet at a given position, there are no previously characterized ZFPs that specifically bind a target site including the triplet at the given position, but there are one or more previously characterized ZFPs that specifically bind to the triplet at a different position, then the triplet is assigned a score of 8. If for a given triplet and a given position, there are no previously characterized ZFPs that bind the triplet either at the given position or another position, the triplet and position are assigned a value 1. The values 10, 8 and 1 are only illustrative, and other values could be used. Furthermore, a more sophisticated assignment of values can be used which also takes into account different binding affinities, specificities and presence of D-able sites, among other factors. In such a scheme, combinations of triplets and positions for which prior ZFPs exist with strong binding affinities are typically given higher values than combinations of triplet and positions for which there are prior ZFPs with lower binding affinities. The selection of potential target sites within a larger sequence and calculation of scores is typically performed by a suitably programmed computer, which outputs one or more potential target site(s) with their score(s). Optionally, user input can be provided to such a computer to specify how many potential target sites should be output. For example, the user can elect to have n potential target sites with the highest scores output, where n is at the discretion of the user. The user can also specify a threshold score, which must be equaled or exceeded for a potential target site to be output.

In a variation of the above method, a potential target site can be evaluated based both on values in a correspondence table and on the presence of one or more D-able subsites. Such is achieved by user input of a context parameter to provide a scaled score for one or more combinations of triplet and a particular position, if the context of the triplet indicates presence of a D-able subsite. For example, a triplet 5'NNG3' followed by an A does not provide a D-able subsite. However, 5'NNG3' followed by a K does provide a D-able site. The user can elect to input a context parameter that increases the value of the subscore for the 5'NNG3' triplet when 5'NNG3' is followed by a K. The scaled subscore for this triplet is then combined with subscores or scaled subscores for other triplets to give an overall score for a potential target site.

In a further variation, a computer performing the above analysis is programmed to output certain target segments receiving high scores in pairs determined by their physical proximity to each other. Paired target segments both of which receive high scores that occur within about five bases of each other are appropriate targets for the design of six-finger zinc proteins formed by linkage of two component zinc finger proteins each having three fingers.

Potential target sites identified by the above methods can be subject to further evaluation or can be used directly for design or selection (if needed) and production of zinc finger proteins. Zinc finger proteins can be designed and synthesized to such target sites using the same methods described for potential target segments containing D-able subsites described above.

V. Database Design of ZFPs

The invention provides methods for design of ZFPs to a preselected target site. These methods are suitable for use in conjunction with the methods of target site selection described above, or by other methods of target site selection.

In designing a new ZFP, it is generally advantageous to make use of information inherent in precharacterized ZFPs and their target sites thereby minimizing the need for de novo design or selection. As with target site selection, several factors are involved in this process. Design is facilitated when, for each triplet subsite in a target site, fingers are not only available in existing ZFPs, but such fingers also contact their respective triplet subsites from the same location in the existing proteins as in the proposed design. For example, consider three existing pairs of ZFP and target site: 5'GCG TGG GAC3', bound by a ZFP with fingers F1-F2-F3 (where F3 interacts with GCG, F2 with TGG, and F1 with GAC), 5'AAG GAG GTG3', bound by a ZFP with fingers F4-F5-F6, and 5'CCG TGA GCA3', bound by a ZFP with fingers F7-F8-F9, and a target site 5'GCG GAG GCA3' for which a ZFP is to be designed. In this situation, the novel protein F7-F5-F3 binds to 5'GCG GAG GCA3' with each finger in the novel protein occurring in the same relative position in the novel protein as it did in the database proteins from which it was obtained. This design is advantageous because the analogous environment of each finger in the novel ZFP with that of its previous ZFP means that the finger is likely to bind with similar specificity and affinity in the novel ZFP as in the parent. Thus, the general rule that the binding characteristics of a zinc finger protein are the aggregate of its component fingers is likely to hold.

Novel zinc finger proteins can also be designed from component fingers that are available in existing proteins, but not at the same positions as in the protein to be designed. For example, using the set of existing ZFP-site pairs described above, the protein F3-F7-F5 can be designed to bind sequence 5'GAG GCA GCG3'. In the novel protein, the fingers occupy different positions than in their respective parental proteins. Although to an approximation a given finger retains its triplet specificity and affinity irrespective of which position it occupies in a ZFP, in practice, contextual effects are more likely to cause changes in specificity and/or affinity of a finger for its triplet subsite when the finger occupies different positions in different zinc finger proteins. Therefore, although ZFPs formed from component fingers occupying different positions than in previously characterized ZFPs typically still bind to the site, the specificity or affinity is sometimes different (typically lower) than expected.

Finally, for preselected target sites including a triplet for which no preexisting finger is available, completely novel fingers can be designed or selected using rules-based approaches or phage display.

The invention provides methods of systematically using a database containing information about existing ZFPs in the design of new ZFPs for a preselected target site according to the principles described above. The organization of a typical database is shown in Table 9. The database typically includes designations for each of a collection of precharacterized ZFPs. The ZFPs can be natural ZFPs or variant ZFPs. The designation can be, for example, the name or a symbol representing each ZFP. The database also includes subdesignations for each of the fingers in a ZFP. Typically, the subdesignations are in the form of amino acid residues occupying selected positions in a finger or fingers. For example, in Table. 9 the subdesignations are the amino acids occupying positions −1 through +6 according to conventional numbering. The database further includes a target nucleic acid segment bound by each zinc finger protein. The nucleic acid segment usually includes three triplets of three bases. The three triplets of bases can be included joined as one sequence or as separate sequences. If bases in a nine base target site are numbered consecutively from the 5' end, a first triplet occupies bases 7–9, a second triplet occupies bases 4–6 and a third triplet occupies bases 1–3. According to this designation of triplet position within a target segment, the first finger of a zinc finger protein (i.e., closest to N-terminus) binds to the first triplet, the second finger to the second triplet, and the third finger to the third triplet. The database can also include additional information such as the binding affinity or dissociation constant of a ZFP for its target site, although such is not essential.

A target site is provided for design of a zinc finger protein using the database. In some methods, the target site is provided by user input. In other methods, the target site is provided as output from any of the methods of target site selection described above. The target site typically comprises at least 9 bases forming at least three triplets. The three component triplets are designated first, second and third triplets respectively occupying bases 7–9, 4–6 and 1–3 of the target site, with the 5' base being assigned as base 1. For the first triplet in the target site, the computer searches the database for a zinc finger protein(s) containing fingers that bind to the triplet. The computer stores records relating to the zinc finger protein(s) thereby identified, and their finger(s) that bind to the first triplet. Optionally, the computer distinguishes between zinc finger proteins containing a finger that binds to the first triplet of the target site at the first finger position and in other positions. If so, the computer stores the two subsets of zinc finger protein(s) as separate records. The process is then repeated for the second triplet in the target site. The computer identifies zinc finger protein(s) containing a finger that specifically binds to the second triplet. Optionally, the computer distinguishes between zinc finger(s) that bind the second triplet from the second position of an existing zinc finger protein or at a different position. Finally, the computer identifies zinc finger protein(s) containing a finger that specifically binds to the third triplet of the target site. Optionally, the computer distinguishes between zinc finger(s) that bind the third triplet from the third position of an existing zinc finger protein or from another position. After searching for ZFPs that bind to each of the first, second and third triplets in the target segment, the computer outputs designations for the ZFPs that have been identified and subdesignations of the fingers that bind to the first, second and third triplets. Optionally, the computer provides separate output of a subset of ZFPs that bind the first triplet from the first finger position, and a subset of ZFPs that bind the first triplet from other positions; and corresponding subsets of ZFPs that bind the second triplet from the second finger position and from other positions, and of ZFPs that bind the third triplet from the third finger position and from other positions.

The information output by the computer can be used in the design and synthesis of novel zinc finger proteins that bind to a preselected target. For example, if the output includes a ZFP1 with a finger X that binds the first triplet of the target, ZFP2 that includes a finger Y that binds to the second triplet of the target, and ZFP3 that includes a finger Z that binds to the third triplet of the target, a novel ZFP can be synthesized comprising the fingers XYZ in that order (N-terminal to C-terminal). If the computer outputs multiple different zinc finger proteins that contain multiple different fingers that bind to a given triplet, the user can select between the fingers depending on whether a finger binds to a particular triplet position from the same position in the database protein as in the ZFP to be designed. For example, a ZFP1 containing fingers XYZ, in which X binds to a first triplet in a target site is generally preferred to a ZFP2 containing fingers ABC, in which finger C binds to the first triplet in a target site. Thus one would typically use finger X rather than C to occupy the first finger position in a ZFP designed to bind the target segment. Often the computer program identifies two ZFPs, each containing a finger that binds a particular triplet, and in each ZFP, the finger occupies the same position in the database protein from which it derives as in the intended design ZFP. In such cases, one often chooses between the two fingers based on the binding affinity for their respective targets, with higher binding affinity being preferred. Optionally, the computer also provides output of proposed amino acid substitutions to one or more fingers for the corresponding triplet(s) bound by the finger(s).

Although database analysis is primarily illustrated for precharacterized zinc finger proteins having three fingers, such databases can alternatively or additionally store information concerning zinc finger proteins with fewer or greater numbers of fingers. Likewise, such databases can be used in the design of zinc finger proteins having fewer or greater than three fingers. For example, some databases of the invention store information concerning ZFPs with only two fingers as well as or instead of information concerning ZFPs with three fingers. ZFPs with only two fingers have corresponding target sites with only two triplets. The information relating to two-finger ZFPs can be used in the design of three-finger ZFPs that bind to nine base target sites in essentially the same manner described above. However, there is no exact correspondence between the relative positions of two fingers in a two-finger protein with the relative positions of three fingers in a three-finger zinc finger protein. This issue can be addressed in two ways. First, all fingers in a two-finger protein can be effectively treated as occupying different positions than fingers in a three-finger protein. Accordingly, if a two finger protein contains a finger that binds to a given triplet, the computer outputs this information and indicates that the finger does not occur at the same position in the database two-finger protein as in the three-finger protein to be designed. Alternatively, the first (N-terminal) finger in a two-finger protein can be considered the equivalent of either the first or second finger in a three-finger protein. The second finger in a two-finger protein can be considered the equivalent of either the second or third finger in a three-finger protein. Accordingly, if the computer identifies a two finger protein with a first (N-terminal) finger binding to a first triplet in a target site for which a zinc finger protein is to be designed, the computer can output that the two finger protein supplies an appropriate finger and at the same position in the database protein as in the three finger protein to be designed.

VII. Production of ZFPs

ZFP polypeptides and nucleic acids encoding the same can be made using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, nucleic acids less than about 100 bases can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.). Similarly, peptides can be custom ordered from any of a variety of sources, such as PeptidoGenic (pkim@ccnet.com), HTI Bio-products, inc. (http://www.hti-bio.com), BMA Biomedicals Ltd (U.K.), Bio. Synthesis, Inc. Oligonucleotides can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either denaturing polyacrylamide gel electrophoresis or by reverse phase HPLC. The sequence of the cloned genes and synthetic oligonucleotides can be verified after cloning using, e.g., the chain termination method for sequencing double-stranded templates of Wallace et al., *Gene* 16:21–26 (1981).

Figure 3:
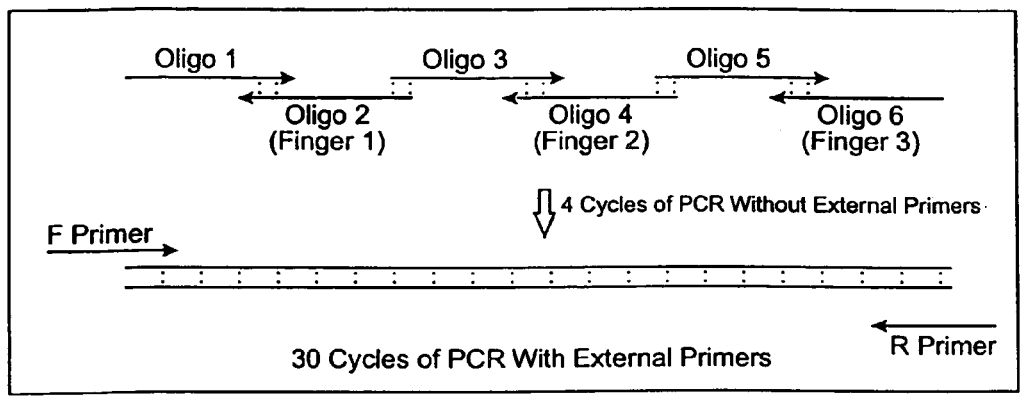
FIG. 3 shows the process of assembling a nucleic acid encoding a designed ZFP.

Two alternative methods are typically used to create the coding sequences required to express newly designed DNA-binding peptides. One protocol is a PCR-based assembly procedure that utilizes six overlapping oligonucleotides (FIG. 3). Three oligonucleotides (oligos 1, 3, and 5 in FIG. 3) correspond to "universal" sequences that encode portions of the DNA-binding domain between the recognition helices. These oligonucleotides typically remain constant for all zinc finger constructs. The other three "specific" oligonucleotides (oligos 2, 4, and 6 in FIG. 3) are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the above-mentioned protocol. The complementary oligos to the common oligos 1 and finger 3 are engineered to leave overhanging sequences specific for the restriction sites used in cloning into the vector of choice in the following step. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment. Alternatively, changes to ZFP recognition helices can be created usingconventional site-directed mutagenesis methods.

Both assembly methods require that the resulting fragment encoding the newly designed ZFP be ligated into a vector. Ultimately, the ZFP-encoding sequence is cloned into an expression vector. Expression vectors that are commonly utilized include, but are not limited to, a modified pMAL-c2 bacterial expression vector (New England BioLabs or an eukaryotic expression vector, pcDNA (Promega). The final constructs are verified by sequence analysis.

Any suitable method of protein purification known to those of skill in the art can be used to purify ZFPs of the invention (see, Ausubel, supra, Sambrook, supra). In addition, any suitable host can be used for expression, e.g., bacterial cells, insect cells, yeast cells, mammalian cells, and the like.

Expression of a zinc finger protein fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the tac promoter (NEB). Bacteria containing the MBP-ZFP fusion plasmids are inoculated in to 2xYT medium containing 110M ZnCl2, 0.02% glucose, plus 50 µg/ml ampicillin and shaken at 37° C. At mid-exponential growth IPTG is added to 0.3 mMand the cultures are allowed to shake. After 3 hours the bacteria are harvested by centrifugation, disrupted by sonication or by passage through a french pressure cell or through the use of lysozyme, and insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 µM ZnCl2, then eluted with maltose in essentially the same buffer (purification is based on a standard protocol from NEB). Purified proteins are quantitated and stored for biochemical analysis.

The dissociation constants of the purified proteins, e.g., Kd, are typically characterized via electrophoretic mobility shift assays (EMSA) (Buratowski & Chodosh, in *Current Protocols in Molecular Biology* pp. 12.2.1–12.2.7 (Ausubel ed., 1996)). Affinity is measured by titrating purified protein against a fixed amount of labeled double-stranded oligonucleotide target. The target typically comprises the natural binding site sequence flanked by the 3 bp found in the natural sequence and additional, constant flanking sequences. The natural binding site is typically 9 bp for a three-finger protein and 2×9 bp+intervening bases for a six finger ZFP. The annealed oligonucleotide targets possess a 1 base 5' overhang which allows for efficient labeling of the target with T4 phage polynucleotide kinase. For the assay the target is added at a concentration of 1 nM or lower (the actual concentration is kept at least 10-fold lower than the than the expected dissociation constant), purified ZFPs are added at various concentrations, and the reaction is allowed to equilibrate for at least 45 min. In addition the reaction mixture also contains 10 mM Tris (pH 7.5), 100 mM KCl, 1 mM MgCl2, 0.1 mM ZnCl2, 5 mM DTT, 10% glycerol, 0.02% BSA. (NB: in earlier assays poly d(IC) was also added at 10–100 µg/µl.)

The equilibrated reactions are loaded onto a 10% polyacrylamide gel, which has been pre-run for 45 min in Tris/ glycine buffer, then bound and unbound labeled target is resolved by electrophoresis at 150V. (alternatively, 10–20% gradient Tris-HCl gels, containing a 4% polyacrylamide stacker, can be used) The dried gels are visualized by autoradiography or phosphorimaging and the apparent Kd is determined by calculating the protein concentration that gives half-maximal binding.

The assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

IX. Applications of Designed ZFPs

ZPFs that bind to a particular target gene, and the nucleic acids encoding them, can be used for a variety of applications. These applications include therapeutic methods in which a ZFP or a nucleic acid encoding it is administered to a subject and used to modulate the expression of a target gene within the subject (see copending application Townsend & Townsend & Crew Ser. No. 09/229,037, filed Jan. 12, 1999). The modulation can be in the form of repression, for example, when the target gene resides in a pathological infecting microorganisms, or in an endogenous gene of the patient, such as an oncogene or viral receptor, that is contributing to a disease state. Alternatively, the modulation can be in the form of activation when activation of expression or increased expression of an endogenous cellular gene can ameliorate a diseased state. For such applications, ZFPs, or more typically, nucleic acids encoding them are formulated with a pharmaceutically acceptable carrier as a pharmaceutical composition.

Pharmaceutically acceptable carriers are determined in part by the particular composition being administered, as well as by the particular method used to administer the composition. (see, e.g., *Remington's Pharmaceutical Sciences,* 17th ed. 1985)). The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and Kd of the particular ZFP employed, the target cell, and the condition of the patient, as well as the body weight or surface area of the patient to be treated. The size of the dose also is determined by the existence, nature, and extent of any adverse side-effects that accompany the administration of a particular compound or vector in a particular patient In other applications, ZFPs are used in diagnostic methods for sequence specific detection of target nucleic acid in a sample. For example, ZFPs can be used to detect variant alleles associated with a disease or phenotype in patient samples. As an example, ZFPs can be used to detect the presence of particular mRNA species or cDNA in a complex mixtures of mRNAs or cDNAs. As a further example, ZFPs can be used to quantify copy number of a gene in a sample. For example, detection of loss of one copy of a p53 gene in a clinical sample is an indicator of susceptibility to cancer. In a further example, ZFPs are used to detect the presence of pathological microorganisms in clinical samples. This is achieved by using one or more ZFPs specific to genes within the microorganism to be detected. A suitable format for performing diagnostic assays employs ZFPs linked to a domain that allows immobilization of the ZFP on an ELISA plate. The immobilized ZFP is contacted with a sample suspected of containing a target nucleic acid under conditions in which binding can occur. Typically, nucleic acids in the sample are labeled (e.g., in the course of PCR amplification). Alternatively, unlabelled probes can be detected using a second labelled probe. After washing, bound-labelled nucleic acids are detected.

ZFPs also can be used for assays to determine the phenotype and function of gene expression. Current methodologies for determination of gene function rely primarily upon either overexpression or removing (knocking out completely) the gene of interest from its natural biological setting and observing the effects. The phenotypic effects observed indicate the role of the gene in the biological system.

One advantage of ZFP-mediated regulation of a gene relative to conventional knockout analysis is that expression of the ZFP can be placed under small molecule control. By controlling expression levels of the ZFPs, one can in turn control the expression levels of a gene regulated by the ZFP to determine what degree of repression or stimulation of expression is required to achieve a given phenotypic or biochemical effect. This approach has particular value for drug development. By putting the ZFP under small molecule control, problems of embryonic lethality and developmental compensation can be avoided by switching on the ZFP repressor at a later stage in mouse development and observing the effects in the adult animal. Transgenic mice having target genes regulated by a ZFP can be produced by integration of the nucleic acid encoding the ZFP at any site in trans to the target gene. Accordingly, homologous recombination is not required for integration of the nucleic acid. Further, because the ZFP is trans-dominant, only one chromosomal copy is needed and therefore functional knock-out animals can be produced without backcrossing.

X. Computer Systems and Programs

Figure 4:
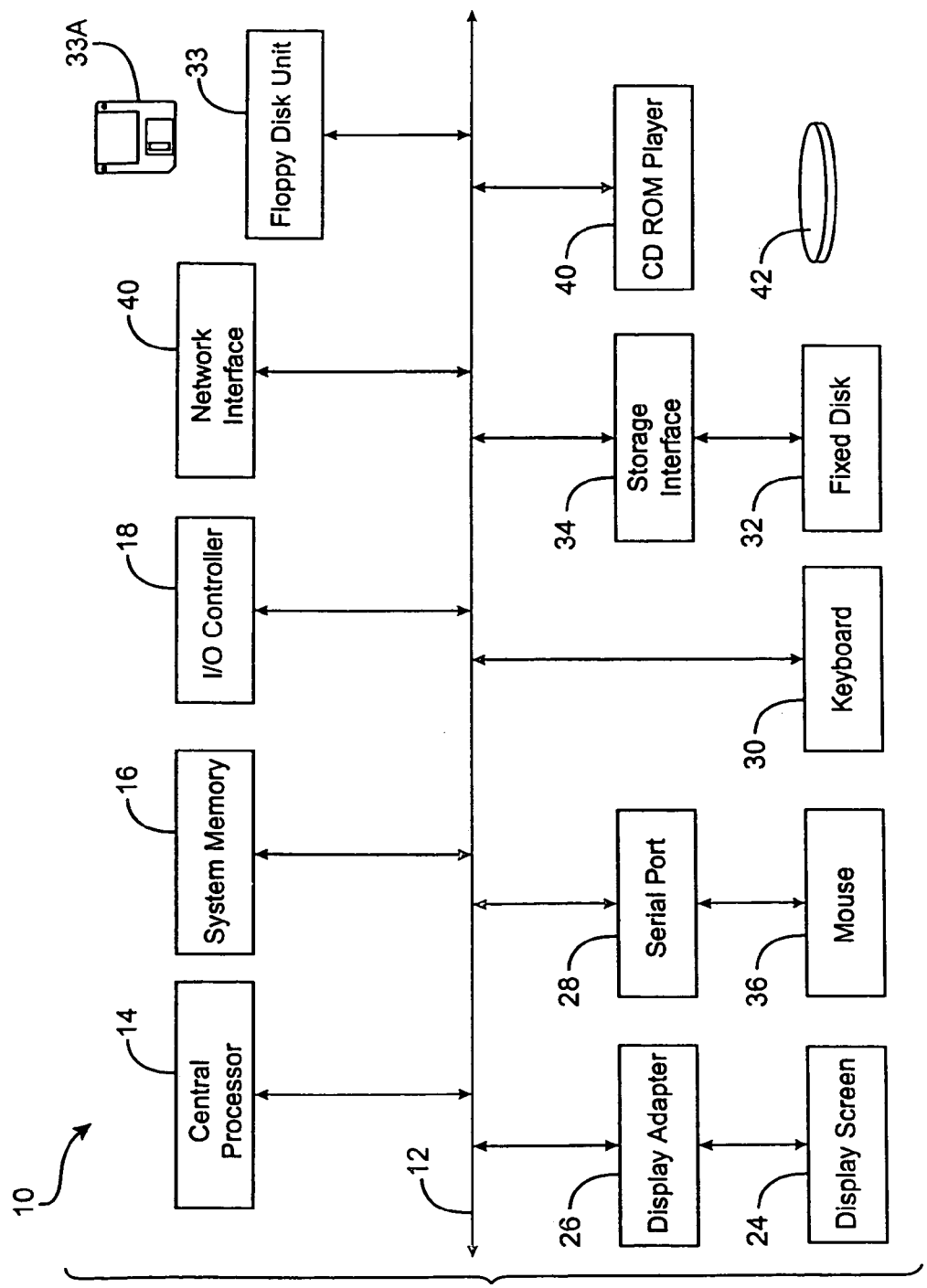
FIGS. 4 and 5 show computer systems for implementing methods of target site selection and zinc finger protein design

FIG. 4 depicts a representative computer system suitable for implementing the present invention. FIG. 4 shows basic subsystems of a computer system 10 suitable for use with the present invention. In FIG. 4, computer system 10 includes a bus 12 which interconnects major subsystems such as a central processor 14, a system memory 16, an input/output controller 18, an external device such as a printer 20 via a parallel port 22, a display screen 24 via a display adapter 26, a serial port 28, a keyboard 30, a fixed disk drive 32 and a floppy disk drive 33 operative to receive a floppy disk 33A. Many other devices can be connected such as a scanner 60 (not shown) via I/O controller 18, a mouse 36 connected to serial port 28 or a network interface 40. Many other devices or subsystems (not shown) may be connected in a similar manner. Also, it is not necessary for all of the devices shown in FIG. 4 to be present to practice the present invention, as discussed below. The devices and subsystems may be interconnected in different ways from that shown in FIG. 4. The operation of a computer system such as that shown in FIG. 4 is readily known in the art and is not discussed in detail in the present application. Source code to implement the present invention may be operably disposed in system memory 16 or stored on storage media such as a fixed disk 32 or a floppy disk 33A.

Figure 5:
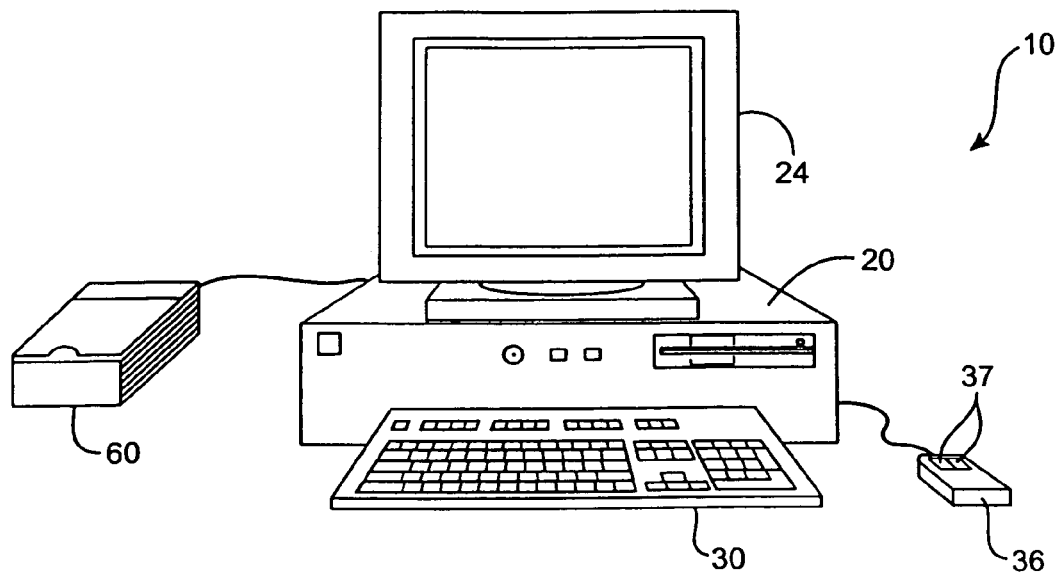

FIG. 5 is an illustration of representative computer system 10 of FIG. 4 suitable for embodying the methods of the present invention. FIG. 5 depicts but one example of many possible computer types or configurations capable of being used with the present invention. FIG. 5 shows computer system 10 including display screen 24, cabinet 20, keyboard 30, a scanner 60, and mouse 36. Mouse 36 and keyboard 30 illustrate "user input devices." Other examples of user input devices are a touch screen, light pen, track ball, data glove, etc.

In a preferred embodiment, System 10 includes a Pentium® class based computer, running Windows® Version 3.1, Windows95® or Windows98® operating system by Microsoft Corporation. However, the method is easily adapted to other operating systems without departing from the scope of the present invention.

Mouse 36 may have one or more buttons such as buttons 37. Cabinet 20 houses familiar computer components such as disk drive 33, a processor, storage means, etc. As used in this specification "storage means" includes any storage device used in connection with a computer system such as disk drives, magnetic tape, solid state memory, bubble memory, etc. Cabinet 20 may include additional hardware such as input/output (I/O) interface 18 for connecting computer system 10 to external devices such as a scanner 60, external storage, other computers or additional peripherals. FIG. 5 is representative of but one type of system for embodying the present invention. Many other system types and configurations are suitable for use in conjunction with the present invention.

Figure 6:
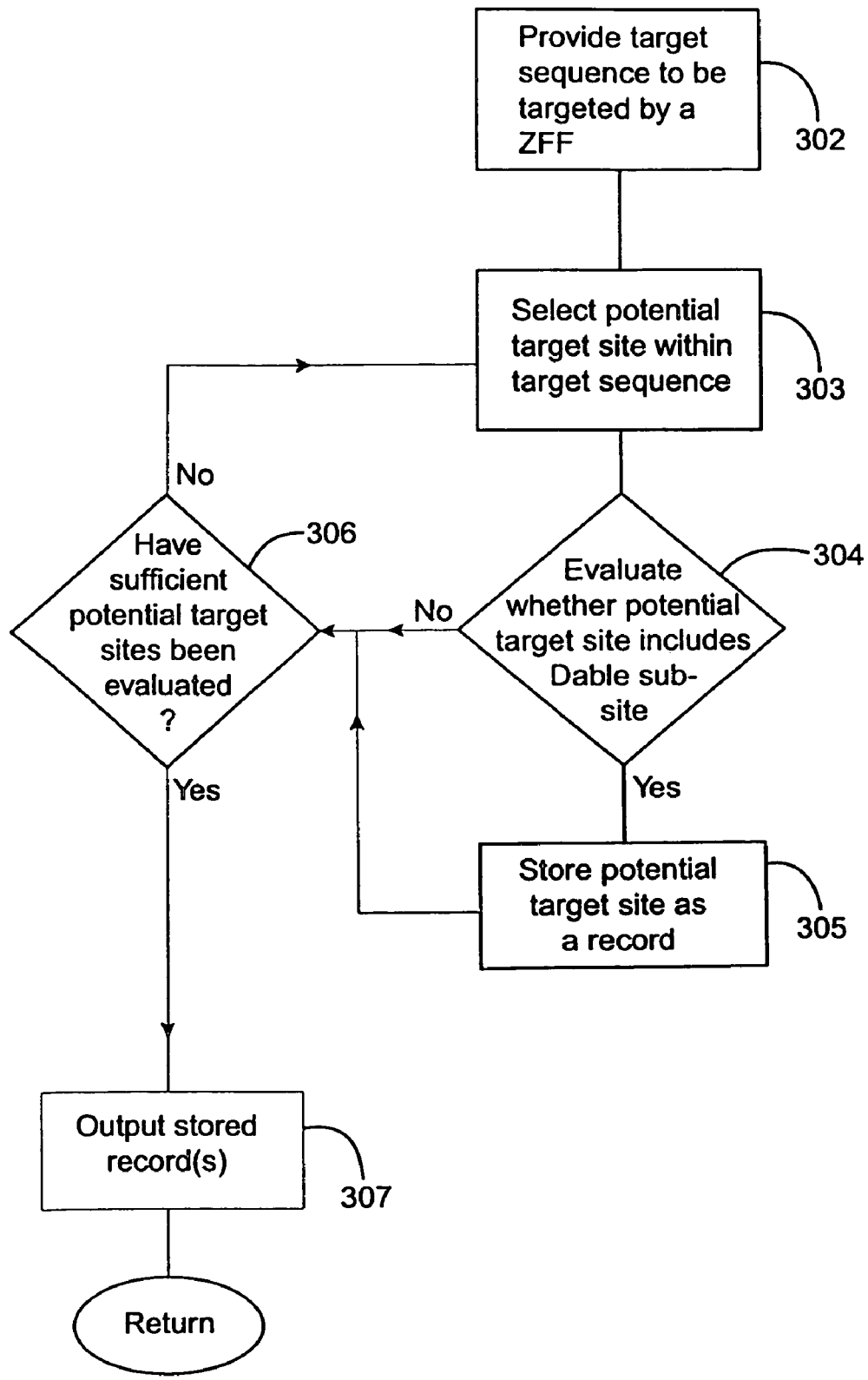
FIG. 6 shows a flow chart of a method for selecting a target site containing a D-able subsite within a target sequence

FIG. 6 depicts a flowchart 301 of simplified steps in a representative embodiment for selecting a target site containing a D-able subsite within a target sequence for targeting by a zinc finger protein. In a step 302, a target sequence to be targeted by a zinc finger protein is provided. Then, in a step 303, a potential target site within the target sequence is selected for evaluation. In a decisional step 304, the potential target site is evaluated to determine whether it contains a D-able subsite. Such a target site conforms to the formula 5'$NNx$ $aNy$ $bNzc$3', wherein wherein each of (x, a), (y, b) and (z, c) is (N, N) or (G, K);
at least one of (x, a), (y, b) and (z, c) is (G, K) and
N and K are IUPAC-IUB ambiguity codes.

Figure 7A:
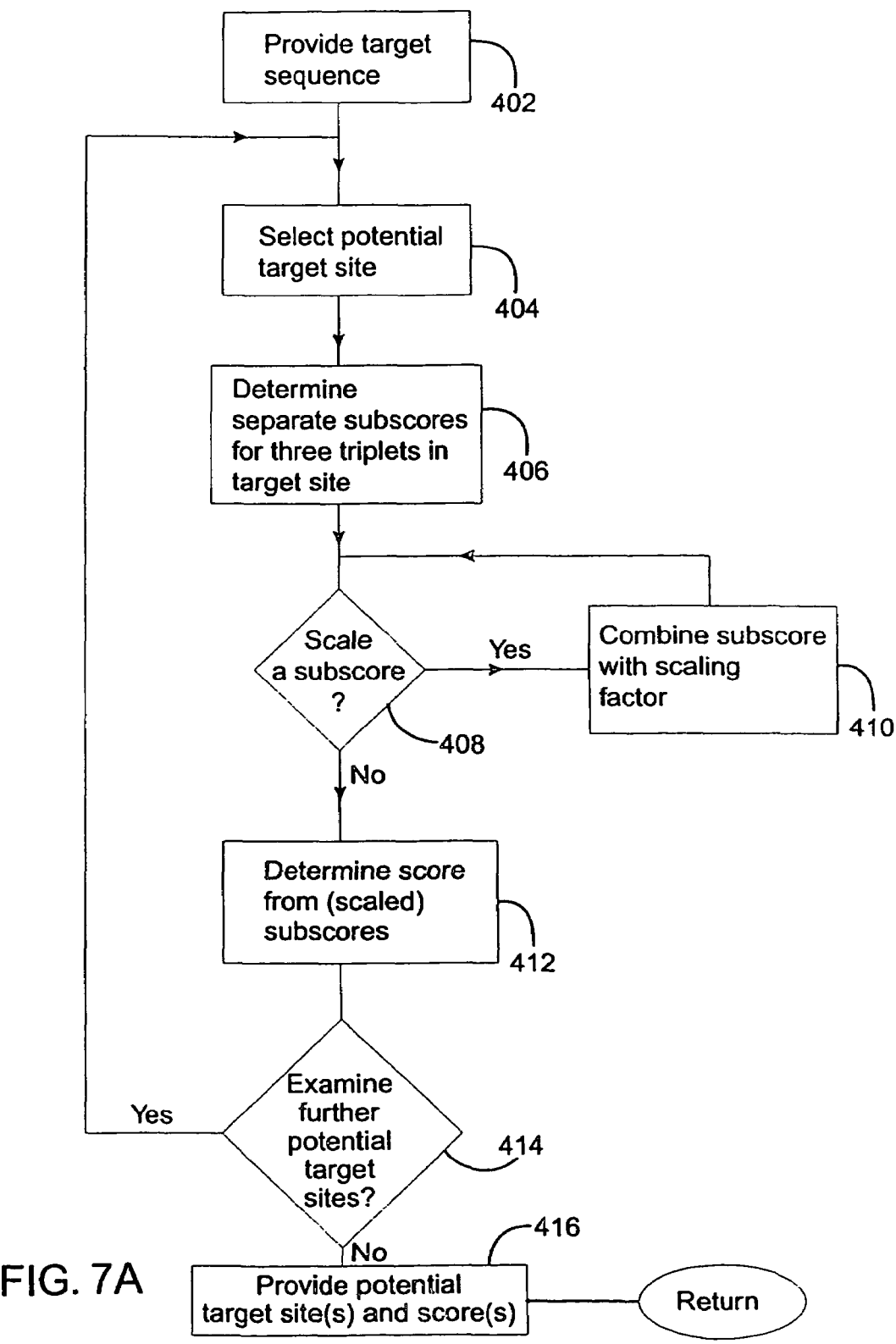
FIG. 7A shows a flow chart for selecting a target site within a target sequence using a correspondence regime.

If the potential target site does contain a D-able subsite, the potential target site is stored as a record in 205. The methods continues with a further decisional step 306. If evaluation of further potential target sites is required by the user, a further iteration of the method is performed starting from 303. If sufficient potential target sites have already been evaluated, records of target sites stored in step 305 are then output in step 307. FIG. 7A depicts a flowchart of simplified steps in another representative embodiment for selecting a target site within a polynucleotide for targeting by a zinc finger protein. In a step 402, a polynucleotide target sequence is provided for analysis. Then, in a step 404, a potential target site within the polynucleotide sequence is selected. The potential target site comprises first, second and third triplets of bases at first, second and third positions in the potential target site. Then, in a step 406, a plurality of subscores are determined by applying a correspondence regime between triplets and triplet position, wherein each triplet has first, second and third corresponding positions, and each corresponding triplet and position is assigned a particular subscore. Next there is an optional decisional step 408 in which the user can elect to scale one or more of the subscores with a scaling factor in step 410. Thereafter in a step 412, a score is determined from the subscores (scaled as appropriate) for the first, second, and third triplets. Then, in a decisional step 414, a check is performed to determine if any further potential target sites are to be examined. If so, then processing continues with step 404. Otherwise, in a step 416, at least one of the potential target sites and its score are provided as output.

Figure 7B:
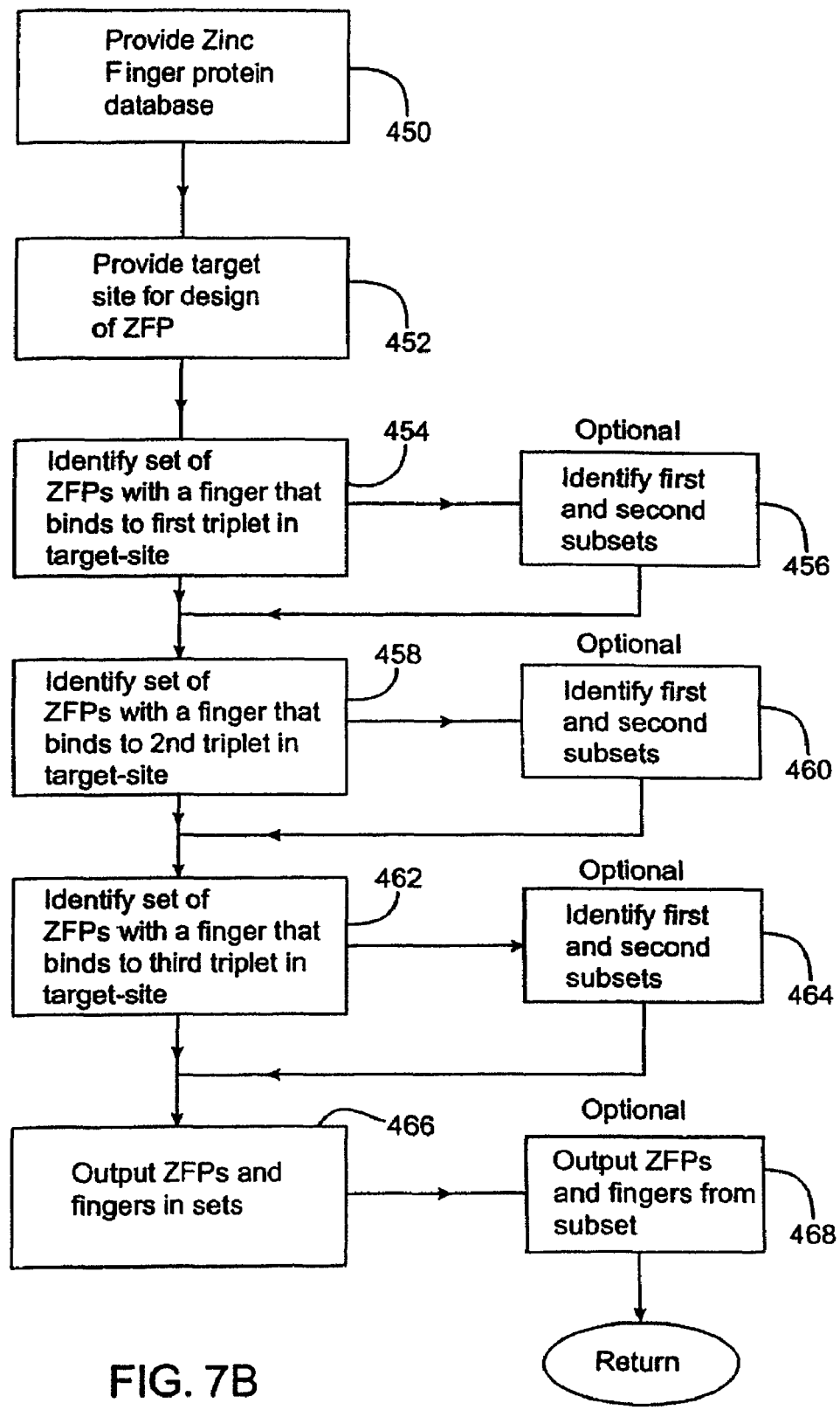
FIG. 7B shows a flow chart for designing a ZFP to bind a desired target site using a database.

FIG. 7B depicts a flowchart of simplified steps in a representative embodiment for producing a zinc finger protein. In a step 450 a database comprising designations for a plurality of zinc finger proteins is provided. Each protein in the database comprises at least first, second and third fingers. The database further comprises subdesignations for each of the three fingers of each of the zinc finger proteins and a corresponding nucleic acid sequence for each zinc finger protein. Each sequence comprises at least first, second and third triplets specifically bound by the at least first, second and third fingers respectively in each zinc finger protein. The first, second and third triplets have an arrangement in the nucleic acid sequence in the same respective order (3'-5') as the first, second and third fingers are arranged in the zinc finger protein (N-terminal to C-terminal).

In a step 452, a target site for design of a zinc finger proteins comprising at least first, second and third triplets is provided. Then, in a step 454, a first set of zinc finger proteins with a finger that binds to the first triplet in the target sequence is identified. There follows an optional step 456 of identifying first and second subsets of the set determined in 454. The first subset comprises zinc finger protein(s)s with a finger that binds the first triplet from the first finger position in the zinc finger protein. The second subset comprises zinc finger protein(s) with a finger that binds the first triplet from other than the first finger position in the zinc finger protein. The method continues at step 458. In this step, a further set of zinc finger proteins is identified, this set comprising a finger that binds to the second triplet in the target site. This step is followed by an optional step 460 of identifying first and second subsets of the set identified in step 458. The first subset comprises zinc finger protein(s) that bind to the second triplet from the second position within a zinc finger protein. The second subset comprises zinc finger protein(s) that bind the second triplet from other than the second position of a zinc finger protein. The method continues at step 462. In 462, a set of zinc finger proteins is identified comprising a finger that binds to the third triplet of the target site. In an optional step 464, first and second subsets of the set identified in step 462 are identified. The first subset comprises zinc finger protein(s) containing a finger that binds to the third triplet from the third finger position of the zinc finger protein. The second subset comprises zinc finger protein(s) containing a finger that binds to the third triplet from other than the third finger position of the zinc finger protein. The method continues at step 466 in which the sets of zinc finger protein identified in steps 454, 458 and 462 are separately output. There is a further optional step 468 in which the first and second subsets of zinc finger proteins identified in steps 460, 464 and 468 are output.

Figure 8A:
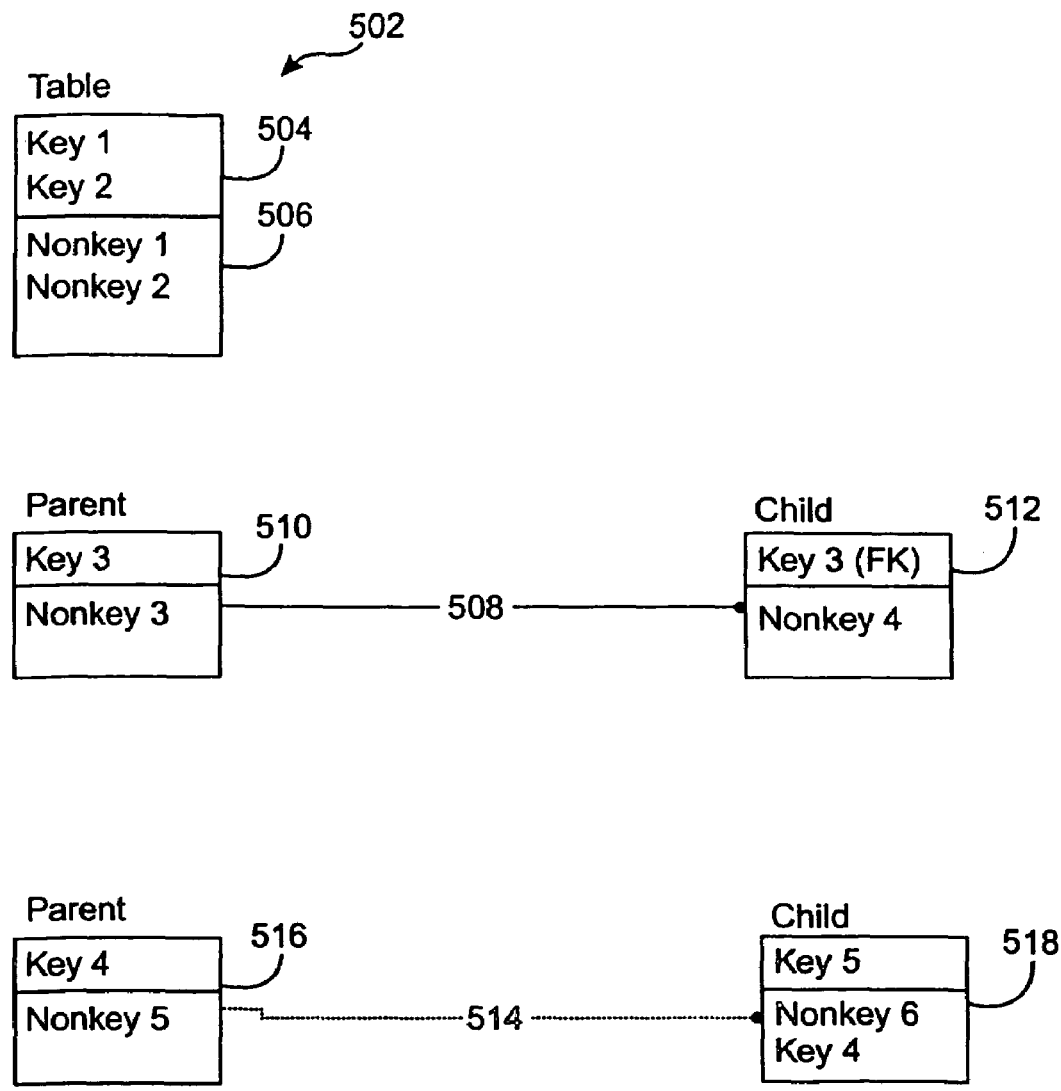
FIG. 8A is an entity representation diagram of a ZFP database.

FIG. 8A is a key to the Entity Representation Diagram (ERD) that will be used to describe the contents of ZFP database. A representative table 502 includes one or more key attributes 504 and one or more non-key attributes 506. Representative table 502 includes one or more records where each record includes fields corresponding to the listed attributes. The contents of the key fields taken together identify an individual record. In the ERD, each table is represented by a rectangle divided by a horizontal line. The fields or attributes above the line are key while the fields or attributes below the line are non-key fields. An identifying relationship 508 signifies that the key attribute of a parent table 510 is also a key attribute of a child table 512. A non-identifying relationship 514 signifies that the key attribute of a parent table 516 is also a non-key attribute of a child table 518. Where (FK) appears in parenthesis, it indicates that an attribute of one table is a key attribute of another table. For both the non-identifying and the identifying relationships, one record in the parent table corresponds to one or more records in the child table.

Figure 8B:
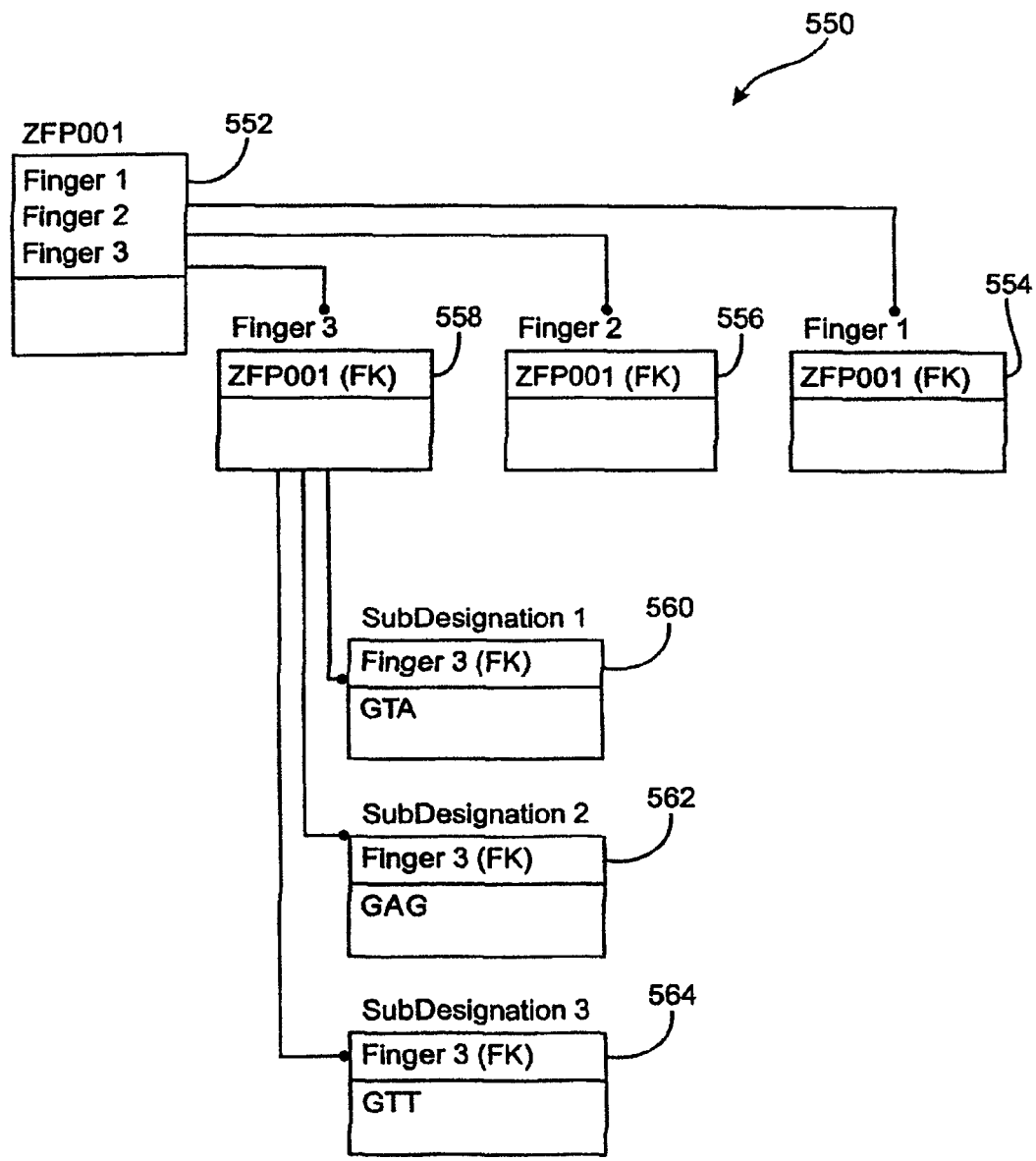
FIG. 8B is a representation of a ZFP database.

FIG. 8B depicts a representative ZFP database 550 according to a particular embodiment of the present invention. Database 550 can typically include designations for each of a collection of precharacterized ZFPs. The ZFPs can be natural ZFPs or variant ZFPs. The designation can be, for example, the name or a symbol representing each ZFP. For example, ZFP 552 of database 550 in FIG. 8B is designated "ZFP001." The database 550 also includes subdesignations for each of the fingers in a ZFP, such as subdesignation 554, Finger 1 of ZFP001 552. Typically, the subdesignations are in the form of amino acid residues occupying selected positions in a finger. Further, the ZFPs have subdesignations that are the amino acids occupying positions −1 through +6 according to conventional numbering. The database can further include a target nucleic acid segment bound by each zinc finger protein. The nucleic acid segment usually includes three triplets of three bases. The three triplets of bases can be included joined as one sequence or as separate sequences. If bases in a nine base target site are numbered consecutively from the 5' end, a first triplet occupies bases 7–9, a second triplet occupies bases 4–6 and a third triplet occupies bases 1–3. According to this designation of triplet position within a target segment, the first finger of a zinc finger protein (i.e., closest to N-terminus) binds to the first triplet, the second finger to the second triplet, and the third finger to the third triplet. The database can also include additional information such as the binding affinity or dissociation constant of a ZFP for its target site, although such is not essential. Further database 550 can include other arrangements and relationships among the ZFPs, fingers and nucleic acids than are depicted in FIG. 8B without departing from the scope of the present invention.

EXAMPLES

Example 1

Search Protocols for DNA Motifs

This Example illustrates how a target segment is selected from a longer gene. The search procedure is implemented using a computer program that allows one to specify one or more DNA sequence motifs in a search protocol. Normal procedure is to input the DNA sequence of a gene or cDNA and then search the sequence multiple times for different motifs, from the most to the least desirable. Thus, of the exemplary protocols listed below one would typically perform protocol 1 first, and if that fails to yield an adequate number of potential target segments, one then tries protocol 2, and so forth.

Protocol 1 searches a target gene for a target site formed from two separate segments, each of 9 or 10 bases. The two segments can be separated by zero to three intervening bases. Each segment includes a D-able subsite of the form NNGG (shown in bold). Each three base subsite within a segment begins with a G. The target sites identified by this analysis can be used directly for ZFP design or can be subject to further analysis, for example, to identify which target segments possess additional D-able subsites. In a target site formed from two segments, each of ten bases, a total of six D-able subsites can be present. All target sites below are shown from 5' to 3' and the nomenclature "0,3" indicates that 0–3 nucleotide of any type may be present.

GNGGNNGNN(N){0,3}GNGGNNGNNN
(SEQ ID NOS:15 and 16)

GNGGNNGNN(N){0,3}GNNGNGGNNN
(SEQ ID NOS:17 and 18)

GNGGNNGNN(N){0,3}GNGGNNGNGG
(SEQ ID NOS:19 and 20)

GNNGNGGNN(N){0,3}GNGGNNGNNN
(SEQ ID NOS:21 and 22)

```
            -continued
GNNGNGGNN(N){0,3}GNNGNGGNNN
(SEQ ID NOS:23 and 24)

GNNGNGGNN(N){0,3}GNGGNNGNGG
(SEQ ID NOS:25 and 26)

GNNGNNGNGG(N){0,3}GNGGNNGNNN
(SEQ ID NOS:27 and 28)

GNNGNNGNGG(N){0,3}GNNGNGGNNN
(SEQ ID NOS:29 and 30)

GNNGNNGNGG(N){0,3}GNGGNNGNGG
(SEQ ID NOS:31 and 32)

GNNGNNGNGGNGGNNGNNN
(SEQ ID NO:33)

GNNGNNGNGGNNGNGGNNN
(SEQ ID NO:34)

GNNGNNGNGGNNGNNGNGG
(SEQ ID NO:35)
```

Protocol 2 is a second procedure for evaluating target sites within a target gene. This procedures again searches for a target site formed from two segments, each of 9 or 10 bases. Each segment contains at least one D-able subsite of the form KNGG. Protocol 2 differs from protocol 1 in that protocol 2 does not require that three base subsites being with a G. Rather in protocol 2, three bases subsites beginning with either a G or T (K in IUBPAC-IUB ambiguity code). Target sites are shown from 5' to 3', and the symbolds "(0,3) and (0,2) indicate intervening segments of 0–3 and 0–2 bases respectively.

```
KNGGNNKNN(N){0,3}KNGGNNKNNN  (SEQ ID NOS:36 and 37)

KNGGNNKNN(N){0,3}KNNKNGGNNN  (SEQ ID NOS:38 and 39)

KNGGNNKNN(N){0,3}KNNKNNKNGG  (SEQ ID NOS:40 and 41)

KNNKNGGNN(N){0,3}KNGGNNKNNN  (SEQ ID NOS:42 and 43)

KNNKNGGNN(N){0,3}KNNKNGGNNN  (SEQ ID NOS:44 and 45)

KNNKNGGNN(N){0,3}KNNKNNKNGG  (SEQ ID NOS:46 and 47)

KNNKNNKNGG(N){0,2}KNGGNNKNNN (SEQ ID NOS:48 and 49)

KNNKNNKNGG(N){0,2}KNNKNGGNNN (SEQ ID NOS:50 and 51)

KNNKNNKNGG(N){0,2}KNNKNNKNGG (SEQ ID NOS:52 and 53)

KNNKNNKNGGNGGNNKNNN          (SEQ ID NO:54)

KNNKNNKNGGNNKNGGNNN          (SEQ ID NO:55)

KNNKNNKNGGNNKNNKNGG          (SEQ ID NO:56)
```

Protocol 3 is the same as protocol two except that protocol three selects target sites with either a KNGG or a KNGT D-able subsite. Target sites are shown from 5'–3'.

```
KNGKNNKNN(N){0,3}KNGKNNKNNN
(SEQ ID NOS:57 and 58)

KNGKNNKNN(N){0,3}KNNKNGKNNN
(SEQ ID NOS:59 and 60)

KNGKNNKNN(N){0,3}KNNKNNKNGK
(SEQ ID NOS:61 and 62)
```

```
            -continued
KNNKNGKNN(N){0,3}KNGKNNKNNN
(SEQ ID NOS:63 and 64)

KNNKNGKNN(N){0,3}KNNKNGKNNN
(SEQ ID NOS:65 and 66)

KNNKNGKNN(N){0,3}KNNKNNKNGK
(SEQ ID NOS:67 and 68)

KNNKNNKNGK(N){0,2}KNGKNNKNNN
(SEQ ID NOS:69 and 70)

KNNKNNKNGK(N){0,2}KNNKNGKNNN
(SEQ ID NOS:71 and 72)

KNNKNNKNGK(N){0,2}KNNKNNKNGK
(SEQ ID NOS:73 and 74)

KNNKNNKNGKNGKNNKNNN (SEQ ID NO:75)

KNNKNNKNGKNNKNGKNNN (SEQ ID NO:76)

KNNKNNKNGKNNKNNKNGK (SEQ ID NO:77)
```

Protocol 4 is more general than any of the protocols described above, and does not require that target sites contain a D-able subsite. Protocol 4 similar requires two segments, each of 9 bases within 0–3 bases of each other of the form GNN GNN GNN. Protocol 5 is the same as protocol 4 except that it searches for target sites formed from two target segments of formula 5'KNN KNN KNN3' within 0–3 bases of each other.

Example 2

This example illustrates that zinc finger proteins that bind to target segments including at least one D-able subsite generally bind with higher affinity than zinc finger proteins binding to target segments lacking D-able subsites provided the ZFP has a D residues at position +2. Fifty-three ZFPs, each having three fingers, were selected from a collection without regard to binding affinity or binding to a D-able subsite. The dissociation constants of the selected ZFPs were determined by binding of the ZFPs to a target segment comprising three contiguous nucleotide triplets respectively bound by the three fingers of the ZFP plus at least one flanking base from the target sequence on either side. All ZFPs had the human Sp1 framework. The binding affinities of these 53 ZFPs were arbitrarily divided into 4 groups, listed as Kd values in Table 2.

TABLE 2

| Dissociation Constants (Kd) | | | |
|---|---|---|---|
| >1,000 nM | 100–1,000 nM | 10–99 nM | < or = 10 nM |
| 31 | 8 | 11 | 3 |

According to this classification only about 25% (14/53) of these proteins had high affinities (Kd less than or equal to 100 nM) for their respective targets. Of these 14 proteins, all had had least one D-able subsite within the target.

Example 3

We searched the sequence of the soybean (*Glycine max*) FAD2-1 cDNA for paired proximate 9 base target segments using protocols 2 and 3. Five targets segments were chosen, and either one or two ZFPs were designed to bind to each of the targets. The targets chosen and the Kd values for the respective designed ZFPs are shown in Table 3. D-able subsites are shown in bold. Sequences are shown from 5' to 3'.

TABLE 3

| TARGET NAME | SEQUENCE | PROTEIN NAME | Kd (nM) | SEQ ID NO: |
|---|---|---|---|---|
| FAD 1 | GAG GTA GAG G | FAD 1A | 10 | 78 |
| FAD 1 | GAG GTA GAG G | FAD 1B | 10 | 78 |
| FAD 2 | GTC GTG TGG A | FAD 2A | 100 | 79 |
| FAD 3 | GTT GAG GAA G | FAD 3A | 100 | 80 |
| FAD 3 | GTT GAG GAA G | FAD 3B | 100 | 80 |
| FAD 4 | GAG GTG GAA G | FAD 4A | 10 | 81 |
| FAD 4 | GAG GTG GAA G | FAD 4B | 2 | 81 |
| FAD 5 | TAG GTG GTG A | FAD 5A | 10 | 82 |

Of the 8 ZFPs made, all bound with high affinity (Kd less than or equal to 100 nM) to their targets, showing that selecting target with a D-able subsite within a 9 bp target allows one to efficiently design a high affinity ZFP. Moreover, all of the ZFPs binding to target sites with two D-able subsites bound more strongly than ZPFs binding to target sites with only one D-able subsite.

Example 4

This example provides further evidence that D-able subsites confer high binding affinity. Fifty-three target segments were identified by protocol 5 listed above, which does not require that a D-able subsite be present in a target site. Fifty-three ZFPs were designed to bind to these respective sites. Thirty three target segments were identified by protocol 3 above, which does require a D-able subsite, and thirty-three ZFPs were designed to bind to these respective sites. Table 4 compares the Kds of ZFPs designed by the different procedures.

TABLE 4

| Search Protocol | Dissociation Constants (Kd) | | | |
|---|---|---|---|---|
| | >1.000 nM | 100–1.000 nM | 10–100 nM | < or = 10 nM |
| #5 | 31 | 8 | 11 | 3 |
| #3 | 0 | 2 | 15 | 16 |

Table 4 shows that 31 of 33 ZFPs designed by protocol 3 have high binding affinity (Kd less than 100 nM). By contrast, only 14 of 56 ZFPs designed by protocol 5 have high binding affinity. These data show that high affinity ZFPs (Kd<100 nM) can be designed more efficiently to targets if the search protocol includes D-able subsite criteria than if the search protocol does not require a D-able subsite.

Example 5

The the relationship between the affinity of the ZFP and the presence of one or more D-able subsites in the target was analyzed for about 300 designed ZFPs specific mostly to different target sites. In this and subsequent analyses, only one ZFP was included per target site, this being the ZFP with the highest affinity.

Table 5 and FIG. 1 show the average Kd of different categories of ZFP categorized by number and type of D-able subsites in 9 base target site bound. In Table 4, and later in Tables 6, 7 and 8, s.e.m. is standard error of the mean, and n is number of proteins examined.

TABLE 5

| D-able subsite/ 9 base target | Aver Kd | n |
|---|---|---|
| 0 | 828 (±66) | 24 |
| 1 GT | 46 (±226) | 05 |
| 1 GG | 138 (±35) | 34 |
| 2 GT | 100 (±30) | 02 |
| 1 GG + 1 GT | 208 (±198) | 04 |
| 2 GG | 15 (±6) | 22 |

The 22 ZFPs designed to targets with two GG type D-able subsites have the strongest binding affinity with an average Kd=15 nM. Of the 50 ZFPs having a Kd<100 nM, 49 have at least one D-able subsite. The table shows the following conclusion: (1) binding to a target site with one D-able subsite bind more strongly than ZFPs binding to a target site lacking a D-able subsites; (2) ZFPS binding to a target site with two D-able subsites bind more strongly than ZFPs that bind to a target sing with one D-able subsite, and (3) ZFPs with a target site with a GG D-able subsite bind more strongly than ZFPs with a target site with a GT D-able subsite.

Example 6

Another factor affecting binding affinity of designed ZFPs is whether a target site has the form GNN GNN GNN rather than KNN KNN KNN. his example shows that D-able subsites confer high binding affinity even in the context of a GNN GNN GNN motif. For this analysis, we selected a population of 59 ZFPs, each of which binds to a different target site of the form GNN GNN GNN. Table 6 shows the Kd values of designed ZFPs as a function of the presence of D-able subsites with a GNN GNN GNN target.

TABLE 6

| D-able subsites/ 9 bp Target | Average Kd | n |
|---|---|---|
| 0 | 787 (±88) | 17 |
| 1 GG | 66 (±14) | 23 |
| 2 GG | 17 (±7) | 18 |
| 1 GG + 1 GT | 5.5 (±4.5) | 2 |

The presence of a D-able subsite strongly affects binding affinity of a ZFP even when the target fits the GNN GNN GNN motif.

Example 7

This Example provides further evidence that the effect of D-able subsites in conferring increased binding affinity is additive with any effects of G residues in conferring higher binding affinity relative to other residues. For this analysis, we selected 101 zinc finger proteins binding to different target sites from our collection, and classified these target sites by the number of G residues present. The target sites contained from 2–8 G residues in a 9 base sequence. Table 7 shows that in general, the more G residues that are present in a target site, the stronger the binding affinity of the ZFP for that site.

TABLE 7

| # Gs/<br>9 base target | Aver Kd, nM<br>(+/−) s.e.m | n |
|---|---|---|
| 2 | >1000 | 4 |
| 3 | 681 (±158) | 8 |
| 4 | 447 (±84) | 26 |
| 5 | 195 (±58) | 28 |
| 6 | 83 ± (66) | 15 |
| 7 | 46 ± (26) | 9 |
| 8 | 1 | 1 |

We analyzed these data further by asking whether the presence or absence of a D-able subsite affected average Kd values of the designed ZFPs. Each category of 9 base target from Table 7 was subdivided into targets containing or not containing D-able subsites. The result of this analysis is shown in Table 8.

TABLE 8

| | Kd, nM<br>D-able site? | |
|---|---|---|
| G's/Target | minus | plus |
| 3 | 809 ± 191 | 467 ± 273 |
| 4 | 867 ± 87 | 132 ± 5 |
| 5 | 640 ± 169 | 98 ± 39 |
| 6 | >1000 | 8 ± 66 |

The table shows that when target sites having the same number of G residues but different numbers of D-able subsites are compared, the sites including D-able subsite(s) confer higher binding affinity. For 9 base target sites having has 4 or more Gs, the average Kd is approximately 100 nM or less if the target has at least one D-able subsite. Particularly notable is the comparison between target sites having 5 G residues. 5 such target sites lacking a D-able subsite had an average Kd of 640 nM. 23 such target sites with two D-able subsites had an average Kd of 98 nM.

Example 10

The ZFP Prediction Module

This example illustrates selection of a target segment within a target gene using a correspondence regime, and use of a database to design a ZFP that binds to the selected target segment. The ZFP Prediction Module facilitates both the site selection and ZFP design processes by taking as input (i) the DNA sequence of interest (ii) various data tables (iii) design parameters and (iv) output parameters, and providing as output a list of potential ZFP target sites in the sequence of interest and a summary of fingers which have been designed to subsites in each target site. This section will describe program inputs, outputs, and scoring protocols for the program. For clarity, the descriptions will be divided into site selection and design functions.

1. Selection of target sites within the DNA region of interest:

Inputs:
1) The target DNA sequence
2) A scores table listing each of the possible three-base pair subsites and scores for its three possible locations in a 9-bp target site is shown in Table 1. The scores table is provided by the user at run-time and may be customized and updated to reflect the user's most current understanding of the DNA-sequence preferences of the zinc finger motif.
3) A 'ZFP data table' which contains target sites, amino acid sequences, and reference data for existing high-affinity ZFPs. This table is required for this portion of the program only if output parameter (ii) is selected below. An example of a ZFP data table is provided in Table 9.
4) An optional context parameter—the "enhancement factor for 'D-able' triplets"-entered by the user at run-time. This parameter multiplies—by the enhancement factor—the score for any 'xxG' subsite flanked by a 3' G or T.
5) Output parameters—supplied by the user—specifying
   i) the number of target sites to include in the output
   ii) whether the program should specifically highlight those target sites (if any) for which three-finger proteins have already been designed
   iii) whether the program should re-order output target sites according to their relative positions in the input target sequence
   iv) whether the program should highlight targetable pairs of 9-bp DNA sites (adjacent, nonoverlapping site pairs separated by n or fewer bases, where n is typically 5, 4, 3, 2 or 1).

Output: A set of potential target sites in the target DNA sequence ranked by score.

If specified, a list of any target sites for which three-finger proteins have already been designed.

If specified, the list of output sites re-ordered according to location in the input sequence If specified, a list of all targetable pairs of 9-bp DNA sites.

The site selection portion of the program assigns a score to every possible 9-bp sequence in a given target DNA fragment, the score reflecting ease of targetability based on using information from previously designed zinc finger proteins. In evaluating a given 9 base sequence, the program first splits the target into its component subsites, and then consults the scores table to obtain a score for each subsite at its location in the potential target site. Finally, it multiplies the subsite scores to obtain an overall score for the 9-bp target site. For example, using the test sequence 5'AGTGCGCGGTGC3' and the scores table in Table 1, the output sites (5'–3') and scores are

| site | subsites | score |
|---|---|---|
| AGTGCGCGG | AGT GCG CGG | 1 × 10 × 1 = 10 |
| GTGCGCGGT | GTG CGC GGT | 10 × 1 × 10 = 100 |
| TGCGCGGTG | TGC GCG GTG | 10 × 10 × 10 = 1000 |
| GCGCGGTGC | GCG CGG TGC | 10 × 1 × 8 = 80 |

In this example, the best target site is 5'TGC GCG GTG3', with a score of 1000. The program also assigns scores to potential targets in the opposite (antisense) strand, but for the sake of simplicity these sites are ignored in this example.

A optional factor, the "enhancement factor for 'D-able' triplets", can be provided to alter the above scoring protocol to account for the context factor—the D-able contact—in evaluating target sites. If this feature is chosen, the program performs the following check when assigning subsite scores:

If a subsite is of the form xxG, then if the adjacent base (on the 3' side) is T or G, then the score of the xxG subsite is multiplied by the enhancement factor, otherwise, the subsite score remains the same.

(If the subsite is of the form xxA, xxC or xxT, its score also remains unchanged.)

For example, if the user inputs an enhancement factor for 'D-able' triplets of 1.25, then the scores above are adjusted as follows:

| site | subsites | score |
|---|---|---|
| AGTGCGCGGt | AGT GCG CGGt | 1 × 10 × (1 × 1.25) = 12.5 (CGG is D-able) |
| GTGCGCGGTg | GTG CGC GGTg | 10 × 1 × 10 (no D-able subsites) |
| TGCGCGGTGc | TGC GCG GTGc | 10 × (10 × 1.25) × 10 = 1250 (GCG is D-able) |
| GCGCGGTGC# | GCG CGG TGC# | 10 × (1 × 1.25) × 8 = 100 (CGG is D-able) |

(When using this option, the program considers the identity of base immediately to the 3' side of the target site (in lower case). For the last site, this base is undefined in this example and this is noted by placing the pound sign '#' at this position.)

After assigning scores to all 9-base pair sequences in the target DNA, the program then prints out the top scores, with the number of sites outputted determined by the user.

As specified by the user, the program can also provide:
 i. a list of any target sites for which three-finger proteins have already been designed.
 ii the list of output sites re-ordered according to location in the input sequence
 iii a list of all targetable pairs of 9-bp DNA sites (adjacent, nonoverlapping site pairs separated by five, three or fewer bases).

II. Design of Proteins for the Chosen Target Sites

Inputs: Sites from the site-selection portion of the program (or otherwise determined)

The 'ZFPdata table' which contains target sites, amino acid sequences, and reference data for existing high-affinity ZFPs.

An output parameter—supplied by the user—specifying whether the program should restrict its output either:
 i to only those proteins (if any) whose target sites are completely identical to sites in the output, or,
  ii to only those proteins (if any) whose target sites match output sites at two or more of the three-bp subsites.

Output: In the absence of restrictions (i) or (ii):

For each potential 9-base pair target site, a listing of three sets of ZFPs and their component fingers from the ZFP data table which respectively bind to the three triplet subsites within the target site. For each subsite, the set of ZFPs can be subdivided into two subsets. One subset contains ZFPs and their fingers that bind a triplet at a given position from the corresponding finger position in a parental ZFP. The other subset contains ZFPs and their fingers that bind a triplet at a given position from a noncorresponding position within a parental ZFP. A first finger position (N—C) corresponds to a first triplet position 3'–5'.

The ZFP design portion of the program facilitates the design process by allowing the user to rapidly review all fingers known to bind subsites in a given 9-base target site. target. Given the optimal design target from the above example (5'TGCGCGGTG3'), and the short ZFP data table provided in Table 9, the output (in the absence of restrictions (i) or (ii)) would be as follows:

```
           site                    score
           5'TGCGCGGTG             1.00E + 003

ZFPs -- PREVIOUS DESIGN:
ORDERED:
Triplet      3   2   1       F1         F2         F3
[1]          5'TGCGGGGCA  ********  ********  *ERDHLRT

[3]          5'GGGGCGGGG  ********  *RSDELQR  ********

[4]          5'GAGTGTGTG  *RKDSLVR  ********  ********

DISORDERED:
      ********      *RSDELTR[2](3)         ********

********      *RSDERKR[2](1)         ********
```

The 'ordered' output shows that, in the ZFP data table, there is one instance where the TGC subsite is contacted by a zinc finger in the third triplet of a target site. The finger in this case is ERDHLRT (SEQ ID NO:88), and the site is 5'TGCGGGGCA3'. There is also one similar instance for each of the other two subsites—GCG, and GTG. The fingers in these cases are, respectively, RSDELQR (SEQ ID NO:89) and RKDSLVR (SEQ ID NO:90). This information is used to propose the three finger protein F1-RKDSLVR, F2-RSDELQR, F3-ERDHLRT (SEQ ID NO:93) as a design to bind the target 5'TGCGCGGTG3'.

The 'disordered' output shows that there are two cases in the ZFPdata table in which fingers contact a GCG subsite, but not at the center subsite of a target. Rather, in one case GCG is contacted at the 5' end, and the other the 3' end, and in these cases the finger sequences are RSDELTR (SEQ ID NO:91) and RSDERKR (SEQ ID NO:92). These are alternate designs for binding GCG in the target site.

TABLE 1

The scores table

| subsite sequence: | subsite score: location in 9 base site: base pairs # | | | subsite sequence: | subsite score: location in 9 base site: base pairs # | | |
|---|---|---|---|---|---|---|---|
| | 7–9 | 4–6 | 1–3 | | 7–9 | 4–6 | 1–3 |
| AAA | 10 | 8 | 8 | CAA | 8 | 8 | 10 |
| AAG | 8 | 8 | 10 | CAG | 1 | 1 | 1 |
| AAC | 1 | 1 | 1 | CAC | 1 | 1 | 1 |
| AAT | 8 | 10 | 10 | CAT | 1 | 1 | 1 |
| AGA | 10 | 8 | 8 | CGA | 1 | 1 | 1 |
| AGG | 1 | 1 | 1 | CGG | 1 | 1 | 1 |
| AGC | 1 | 1 | 1 | CGC | 1 | 1 | 1 |

TABLE 1-continued

The scores table

| subsite sequence: | subsite score: location in 9 base site: base pairs # | | | subsite sequence: | subsite score: location in 9 base site: base pairs # | | |
|---|---|---|---|---|---|---|---|
| | 7–9 | 4–6 | 1–3 | | 7–9 | 4–6 | 1–3 |
| AGT | 1 | 1 | 1 | CGT | 1 | 1 | 1 |
| ACA | 8 | 10 | 8 | CCA | 1 | 1 | 1 |
| ACG | 1 | 1 | 1 | CCG | 1 | 1 | 1 |
| ACC | 1 | 1 | 1 | CCC | 1 | 1 | 1 |
| ACT | 1 | 1 | 1 | CCT | 1 | 1 | 1 |
| ATA | 8 | 10 | 8 | CTA | 1 | 1 | 1 |
| ATG | 1 | 1 | 1 | CTG | 1 | 1 | 1 |
| ATC | 1 | 1 | 1 | CTC | 1 | 1 | 1 |
| ATT | 1 | 1 | 1 | CTT | 1 | 1 | 1 |
| GAA | 10 | 10 | 10 | TAA | 8 | 8 | 10 |
| GAG | 10 | 10 | 10 | TAG | 10 | 10 | 8 |
| GAC | 10 | 10 | 8 | TAC | 10 | 8 | 10 |
| GAT | 10 | 10 | 10 | TAT | 1 | 1 | 1 |
| GGA | 10 | 10 | 10 | TGA | 10 | 10 | 8 |
| GGG | 10 | 10 | 10 | TGG | 10 | 10 | 10 |
| GGC | 10 | 10 | 10 | TGC | 8 | 10 | 10 |
| GGT | 10 | 10 | 10 | TGT | 10 | 10 | 8 |
| GCA | 10 | 10 | 10 | TCA | 10 | 8 | 8 |
| GCG | 10 | 10 | 10 | TCG | 8 | 10 | 8 |
| GCC | 10 | 10 | 8 | TCC | 10 | 8 | 10 |
| GCT | 10 | 10 | 10 | TCT | 1 | 1 | 1 |
| GTA | 10 | 10 | 10 | TTA | 10 | 10 | 8 |
| GTG | 10 | 10 | 10 | TTG | 8 | 10 | 8 |
| GTC | 10 | 10 | 10 | TTC | 1 | 1 | 1 |
| GTT | 10 | 10 | 10 | TTT | 8 | 10 | 8 |

TABLE 9

Exemplary ZFP data table

| # | target site | ZFP sequence | | | reference information | ZFP SEQ ID NO: |
|---|---|---|---|---|---|---|
| | | F1 | F2 | F3 | | |
| 1 | TGCGGGGCA | RSADLTR | RSDHLTR | ERDHLRT | SBS design GR-223, Kd: 8 nM | 94 |
| 2 | GCGTGGGCG | RSDELTR | RSDHLTT | RSDERKR | Zif 268, Kd: 0.04 nM | 95 |
| 3 | GGGGCGGGG | KTSHLRA | RSDELQR | RSDHLSK | SP1, Kd: 25 nM | 96 |
| 4 | GAGTGTGTG | RKDSLVR | TSDHLAS | RSDNLTR | SBS design GL-8.3.1, Kd: 32 nM | 97 |

Other examples of zinc finger proteins, the sequences of their fingers and target sites bound appropriate for inclusion in such a database are discussed in the references cited in the Background Section.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

What is claimed is:

1. A method of producing a zinc finger protein or a nucleic acid encoding the same, comprising:

(a) providing a database comprising designations for a plurality of precharacterized zinc finger proteins, each protein comprising at least first, second and third fingers, and subdesignations for each of the three fingers of each of the zinc finger proteins, wherein at least one protein in the database has a third finger that is different from the third finger of at least one other protein in the database; a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminal to C-terminal);

(b) providing a preselected target site for design of a zinc finger protein, the target site comprising contiguous first, second and third triplets in a 3'–5' order, (c) for the first, second and third triplet in the target site, identifying first, second and third sets of zinc finger protein(s) in the database, the first set comprising zinc finger protein(s) comprising a finger specifically binding to the first triplet in the target site, the second set comprising zinc finger protein(s) comprising a finger specifically binding to the second triplet in the target site, the third set comprising zinc finger protein(s) comprising a finger specifically binding to the third triplet in the target site;

(d) outputting designations and subdesignations of the zinc finger proteins in the first, second, and third sets identified in step (c); and (e) producing (i) a zinc finger protein that binds to the target site comprising a first finger from a zinc finger protein from the first set, a second finger from a zinc finger protein from the second set, and a third finger from a zinc finger protein from the third set, or (ii) a nucleic acid encoding the zinc finger protein.

2. A method of producing a zinc finger protein or nucleic acid encoding the same comprising:

(a) providing a database comprising designations for a plurality of precharacterized zinc finger proteins, each protein comprising at least first, second and third fingers, and subdesignations for each of the three fingers of each of the zinc finger proteins; a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminal to C-terminal);

(b) providing a preselected target site for design of a zinc finger protein, the target site comprising contiguous first, second and third triplets in a 3'–5, order, (c) for the first, second and third triplet in the target site, identifying first, second and third sets of zinc finger protein(s) in the database, the first set comprising zinc finger protein(s) comprising a finger specifically binding to the first triplet in the target site, the second set comprising zinc finger protein(s) comprising a finger specifically binding to the second triplet in the target site, the third set comprising zinc finger protein(s) comprising a finger specifically binding to the third triplet in the target site;
(d) identifying subsets of the first, second and third sets, the subset of the first set comprising zinc finger protein(s) comprising a finger that specifically binds to the first triplet in the target site from the first finger position of a zinc finger protein in the database; the subset of the second set comprising zinc finger protein(s) comprising a finger that specifically binds to the second triplet in the target site from the second finger position in a zinc finger protein in the database; the subset of the third set comprising zinc finger protein(s) comprising a finger that specifically binds to the third triplet in the target site from a third finger position in a zinc finger protein in the database;
(e) outputting designations and subdesignations of the subset of the first, second and third sets; and
(f) producing (i) a zinc finger protein comprising a first finger from the first subset, a second finger from the second subset, and a third finger from the third subset, or (ii) a nucleic acid encoding the same.

3. The method of claim 2, wherein the outputting comprises outputting the designations and subdesignations of the subsets of the first, second and third sets, and the first, second and third sets minus their respective subsets.

4. The method of claim 1, wherein the target site is provided by user input.

5. The method of claim 1 wherein the target site is provided by
providing a target nucleic acid to be targeted by a zinc finger protein;
selecting a plurality of potential target sites within the target nucleic acid sequence;
evaluating whether each selected target site comprises 5'NNx aNy bNzc3; and
outputting a selected target site within the target nucleic acid comprising 5'NNx aNy bNzc3', the output selected target site providing the target site in step (b) of claim 1, wherein
each of (x, a), (y, b) and (z, c) is (N, N) or (G, K);
at least one of (x, a), (y, b) and (z, c) is (G, K), and
N and K are IUPAC-IUB ambiguity codes.

6. A method of producing a zinc finger protein or a nucleic acid encoding the same, comprising:
(a) providing a database comprising
designations for a plurality of precharacterized zinc finger proteins, each protein comprising at least first and second fingers,
subdesignations for each of the fingers of each of the zinc finger proteins; and a corresponding nucleic acid sequence for each zinc finger protein, each sequence comprising first and second triplets specifically bound by the first and second fingers respectively, the triplets being arranged in the nucleic acid sequence (3'–5') in the same respective order as the first and second and fingers are arranged in the zinc finger protein (N-terminal to C-terminal);
(b) providing a preselected target site for design of a zinc finger protein, the target site comprising contiguous first and second triplets ordered 3'5' in the target site;
(c) for the first and second triplet in the target site, identifying first and second sets of zinc finger protein(s) in the database, the first set comprising zinc finger protein(s) comprising a finger specifically binding to the first triplet in the target site, the second set comprising zinc finger protein comprising a finger specifically binding to the second triplet in the target site;
(d) identifying subsets of the first and second sets, the subset of the first set comprising zinc finger protein(s) comprising a finger that specifically binds to the first triplet in the target site from the first finger position of a zinc finger protein in the database, and the subset of the second set comprising zinc finger protein(s) comprising a finger that specifically binds to the second triplet in the target site from the second finger position in a zinc finger protein in the database;
(e) outputting designations and subdesignations of the zinc finger proteins in the subsets of the first, and second sets identified in step (c); and
(f) producing (i) a zinc finger protein that binds to the target site comprising a first finger from a zinc finger protein from the subset of the first set and a second finger from a zinc finger protein from a subset of the second set, or (ii) a nucleic acid encoding the same.

7. A method of producing a zinc finger protein or a nucleic acid encoding the same, comprising:
(a) providing a database comprising:
designations for a plurality of precharacterized zinc finger proteins, each protein comprising at least first and second fingers;
subdesignations for each of the fingers of each of the zinc finger proteins; and
a corresponding nucleic acid sequence for each zinc finger protein, each sequence comprising first, and second triplets specifically bound by the first and second fingers respectively, the triplets being arranged in the nucleic acid sequence (3'–5') in the same respective order as the first and second and fingers are arranged in the zinc finger protein (N-terminal to C-terminal);
(b) providing a preselected target site for design of a zinc finger protein, the target site comprising contiguous firsts second and third triplets ordered 3'5' in the target site;
(c) for the first and third triplet in the target site, identifying first and second sets of zinc finger protein(s) in the database, the first set comprising zinc finger protein(s) comprising a finger specifically binding to the first triplet in the target site, the second set comprising zinc finger protein(s) comprising a finger specifically binding to the third triplet in the target site;
(d) identifying subsets of the first and second sets, the subset of the first set comprising zinc finger protein(s) comprising a finger that specifically binds to the first triplet in the target site from the first finger position of a zinc finger protein in the database; and the subset of the second set comprising zinc finger protein(s) comprising a finger that specifically binds to the third triplet in the target site from the second finger position in a zinc finger protein in the database;
(e) outputting designations and subdesignations of the subsets of the zinc finger proteins in the first and second sets identified in step (c); and
(f) producing (i) a zinc finger protein that binds to the target site comprising first, second and third fingers, wherein the first finger is from a zinc finger protein from the subset of the first set and the third finger is from a zinc finger protein from the subset of the second set, or (ii) a nucleic acid encoding the same.

8. A computer program product for designing a zinc finger protein comprising:

(a) code for providing a database comprising
  designations for a plurality of precharacterized zinc finger proteins, each protein comprising at least first, second and third fingers, wherein at least one protein in the database has a third finger that is different from the third finger of at least one other protein in the database;
  subdesignations for each of the three fingers of each of the zinc finger proteins;
  a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminus to C-terminus);
(b) code for providing a preselected target site for design of a zinc finger protein, the target site comprising at least first, second and third triplets,
(c) for the first, second and third triplet in the target site, code for identifying first, second and third sets of zinc finger protein(s) in the database, the first set comprising zinc finger protein(s) comprising a finger specifically binding to the first triplet in the target site, the second set comprising zinc finger protein(s) comprising a finger specifically binding to the second triplet in the target site, the third set comprising zinc finger protein(s) comprising a finger specifically binding to the third triplet in the target site;
(d) code for outputting designations and subdesignations of the zinc finger proteins in the first, second, and third sets identified in step (c)
(e) a computer readable storage medium for holding the codes.

9. A system for designing a zinc finger protein comprising:
  (a) a memory;
  (b) a system bus;
  (c) a processor operatively disposed to:
    (1) provide a database comprising
      designations for a plurality of precharacterized zinc finger proteins, each protein comprising at least first, second and third fingers, and subdesignations for each of the three fingers of each of the zinc finger proteins; wherein at least one protein in the database has a third finger that is different from the third finger of at least one other protein in the database;
      a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminus to C-terminus);
    (2) provide or be provided with a preselected target site for design of a zinc finger protein, the target site comprising at least first, second and third triplets,
    (3) for the first, second and third triplet in the target site, identifying first, second and third sets of zinc finger protein(s) in the database, the first set comprising zinc finger protein(s) comprising a finger specifically binding to the first triplet in the target site, the second set comprising zinc finger protein(s) comprising a finger specifically binding to the second triplet in the target site, the third set comprising zinc finger protein(s) comprising a finger specifically binding to the third triplet in the target site;
    (4) output designations and subdesignations of the zinc finger proteins in the first, second, and third sets identified in step (3).

10. The method of claim 1 wherein the target site is provided by
  providing a polynucleotide sequence;
  selecting a potential target site within the polynucleotide sequence; the potential target site comprising contiguous first, second and third triplets of bases at first, second and third positions in the potential target site;
  determining a plurality of subscores by applying a correspondence regime between triplets and triplet position in a sequence of three contiguous triplets, wherein each triplet has first, second and third corresponding positions, and each combination of triplet and triplet position has a particular subscore
  calculating a score for the potential target site by combining subscores for the first, second, and third triplets;
  repeating the selecting, determining and calculating steps at least once on a further potential target site comprising first, second and third triplets at first, second and third positions of the further potential target site to determine a further score;
  providing output of at least one potential target site with its score, the at least one output potential target site providing the preselected target site for step (b) in claim 1.

11. A computer implemented method of designing a zinc finger protein comprising:
  (a) providing a database comprising designations for a plurality of precharacterized zinc finger proteins, each protein comprising at least first, second and third fingers, and subdesignations for each of the three fingers of each of the zinc finger proteins; wherein at least one third finger of the plurality of precharacterized zinc finger proteins is different from at least one other third finger; a corresponding nucleic acid sequence for each zinc finger protein, each sequence comprising at least first, second and third triplets specifically bound by the at least first, second and third fingers respectively in each zinc finger protein, the first, second and third triplets being arranged in the nucleic acid sequence (3'–5') in the same respective order as the first, second and third fingers are arranged in the zinc finger protein (N-terminal to C-terminal);
  (b) providing a target site for design of a zinc finger protein, the target site comprising contiguous first, second and third triplets in a 3'-5' order,
  (c) for the first, second and third triplet in the target site, identifying first, second and third sets of zinc finger protein(s) in the database, the first set comprising zinc finger protein(s) comprising a finger specifically binding to the first triplet in the target site, the second set comprising zinc finger protein(s) comprising a finger specifically binding to the second triplet in the target site, the third set comprising zinc finger protein(s) comprising a finger specifically binding to the third triplet in the target site;
  (d) outputting designations and subdesignations of the zinc finger proteins in the first, second, and third sets identified in step (c).

* * * * *